US006303317B1

(12) United States Patent
Alber et al.

(10) Patent No.: US 6,303,317 B1
(45) Date of Patent: Oct. 16, 2001

(54) PEPTIDE PROBES AND METHODS FOR MAKING THE SAME

(75) Inventors: Thomas C. Alber; Victoria Allen; Shivani Nautiyal, all of Berkeley, CA (US)

(73) Assignee: The Regents of the University of California, Berkeley, CA (US)

( * ) Notice: Subject to any disclaimer, the term of this patent is extended or adjusted under 35 U.S.C. 154(b) by 0 days.

(21) Appl. No.: 09/015,030

(22) Filed: Jan. 28, 1998

Related U.S. Application Data

(60) Provisional application No. 60/036,219, filed on Jan. 28, 1997.

(51) Int. Cl.[7] ..................................................... G01N 33/53

(52) U.S. Cl. ........................... 435/7.1; 530/350; 536/24.3

(58) Field of Search ........................... 530/350; 536/24.3; 435/7.1

(56) References Cited

FOREIGN PATENT DOCUMENTS

| | | |
|---|---|---|
| 94/02505 | 2/1994 | (WO) . |
| 94/16109 | 7/1994 | (WO) . |
| 94/28290 | 12/1994 | (WO) . |
| 96/20953 | 7/1996 | (WO) . |

OTHER PUBLICATIONS

Fairman, et al., *Biochemistry*, 35:2824–2829 (1996).
Lumb, et al., *Biochemistry*, 34:8642–8648 (1995).
Huxley and Kendrew, *Nature*, 170:882–883 (1952).
Pauling and Corey, *Nature*, 171:59–61 (1953).
Crick, *Acta Cryst.*, 6:685–689 (1953).
Crick, *Acta Cryst.*, 6:689–697 (1953).
Lupas, "Coiled Coils: New Structures and New Functions," *TIBS*, 21:375–382 (1996).
Wagner and Green, *Science*, 262:395–399 (1993).
Cohen and Parry, *Proteins*, 7:1–15 (1990).
Wilson et al., *Nature*, 289:366 (1981).
Banner et al., *J. Mol. Biol.*, 196:657–675 (1987).
O'Shea et al., *Science*, 254:539–544 (1991).
Cusack et al., *Nature*, 347:249–255 (1990).
Beck et al., *J. Mol. Biol.*, 231:311–323 (1993).
Lovejoy et al., *Science*, 259:1288–1293 (1993).
Yan et al., *Science*, 262:2027–2030 (1993).
Holberton et al., *J. Mol. Biol.*, 204:789–795 (1988).
Koski et al., *J. Biol. Chem.*, 267:12258–12265 (1992).
Ayer et al., *Cell*, 72:211–222 (1993).
Gauger and Goldstein, *J. Biol. Chem.*, 268:13657–13666 (1993).
Marshal and Holberton, *J. Mol. Biol.*, 231:521–530 (1993).
Zervos et al., *Cell*, 72:223–232 (1993).
Woolfson and Alber, "Predicting Oligomerization States of Coiled Coils," *Protein Science*, 4:1596–1607 (1995).
Berger et al., "Predicting Coiled Coils by Use of Pairwise Residue Correlations,"*Proc. Natl. Acad. Sci. USA*, 92:8259–8263 (1995).
O'Shea, "Mechanism of Specificity in the Fos–Jun Oncoprotein Heterodimer," *Cell*, 68:699–708 (1992).
Lavigne et al., *J. Mol. Biol.*, 254:505–520 (1995).
Kammerer et al., *J. Engel, J. Mol. Biol.*, 250:64–73 (1995).
O'Shea, *Science*, 245:646–648 (1989).
Graddis et al., *Biochemistry*, 32:12664–12671 (1993).
Hodges et al., *J. Biol. Chem.*, 256:1214–1224 (1981).
Nautiyal et al., *Biochemistry*, 34:11646–11651 (1995).
Alber, *Curr. Opin. Genet. Dev.*, 2:205–210 (1992).
O'Shea et al., *Current Biol.*, 3(10):658–667 (1993).
Zhou et al., *J. Mol. Biol.*, 237:500–512 (1994).
Krylov et al., *EMBO J.*, 13:2849–2861 (1994).
Zhu et al., *Int. J. Pept. Protein Res.*, 40:171–179 (1992).
Lupas, *TIBS*, 21:337 (1996).
Vinson et al., *Genes Dev.*, 7:1047–1058 (1993).
Zhou et al., *Prot. Eng.*, 7:1365–1372 (1994).
Lumb et al., *Biochemistry*, 34:8642–8648 (1995).
Zeng et al., *Proc. Natl. Acad. Sci. USA*, 94:3673–3678 (1997).
Monera et al., *Prot. Eng.*, 9:353–363 (1996).
Harbury et al., *Science*, 262:1401–1407 (1993).
Harbury et al., *Nature*, 371:80–83 (1994).
Vieth et al., *J. Mol. Biol.*, 251:448–467 (1995).
Zhu et al., *Prot. Sci.*, 2:383–394 (1993).
Corden et al., *Exp. Dermatol.*, 5:297–307 (1996).
Steinert et al., *Ann. Rev. Cell Biol.*, 1:41–65 (1985).
Caruthers et al., *Nuc. Acids Res. Symp. Ser.* 215–223 (1980).
Horn et al., *Nuc. Acids. Res. Symp. Ser.* 225–232 (1980).
Cionciolo et al., *Immunol. Lett.* 19:7–14 (1988).
Nakamura, *J. Cancer Res. Clinical Onco.*, 121:529–534 (1995).
Munemitsu et al., *Proc. Natl. Acad. Sci. USA*, 92:3046–3050 (1995).
Rubinfeld et al., *Science*, 262:1731–1734 (1993).
Polakis, *Curr. Op. Genetics and Development*, 5:66–71 (1995).
Joslyn et al., *Proc. Natl. Acad. Sci. USA*, 90:11109–11113 (1993).
Groden et al., *Cancer Res.*, 55:1531–1539 (1995).
O'Neil et al., *Science*, 250:646–651 (1990).
Gill and von Hippel, *Anal. Biochem*, 182:319–326 (1989).
Morin et al., *Proc. Natl. Acad. Sci. USA*, 93:7950–7954 (1996).

(List continued on next page.)

*Primary Examiner*—Scott W. Houtteman
(74) *Attorney, Agent, or Firm*—Flehr Hohbach Test Albritton & Herbert LLP; Todd A. Lorenz

(57) ABSTRACT

Methods for creating and using polypeptide probes with high affinity for any desirable coiled coil region are described, as well as heterospecific polypeptide probes directed to the coiled coil region of a target polypeptide. Core residue packing rules are provided for selective amino acid pairing and packing in the hydrophobic core of the interhelical interface.

8 Claims, 6 Drawing Sheets

OTHER PUBLICATIONS

McGregor, *Mol. Biotechnol.*, 6:155–162 (1996).
Janda, *Proc. Natl. Acad. Sci. USA*, 91:10779–10785 (1994).
Goldman et al., *J. Cell Biol.* 134:971–983 (1996).
Olive et al., *J. Biol. Chem.*, 271:2040–2047 (1996).
Olive et al., *J. Biol. Chem.*, 272:18586–18594 (1997).
Sourgen et al., *Eur. J. Biochem.*, 240:765–773 (1996).
Tripet et al., *Prot. Eng.*, 9:1029–1042 (1996).
Smith et al., *Proc. Natl. Acad. Sci. USA*, 90:2846–2850 (1993).
Lu et al., *Nature Structural Biology*, 2:1075–1082 (1995).
Popovic et al., *Science*, 224:497–500 (1984).
Wild et al., "A Synthetic Peptide Inhibitor of Human Immunodeficiency Virus Replication: Correlation Between Solution Structure and Viral Inhibition," *Proc. Natl. Acad. Sci. USA*, 89:10537–10541 (1992).

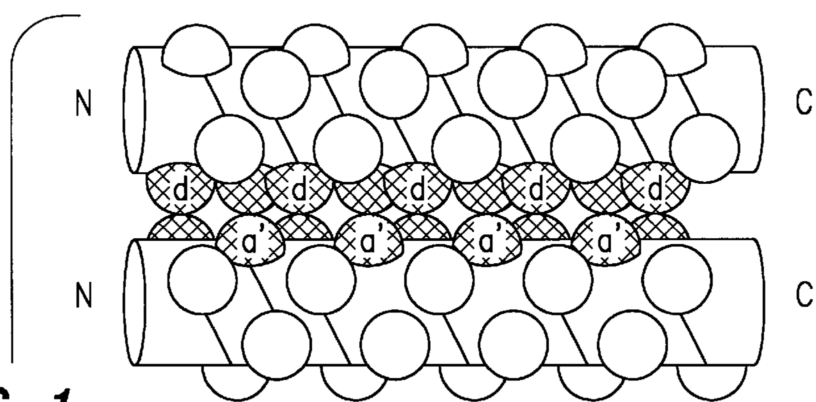
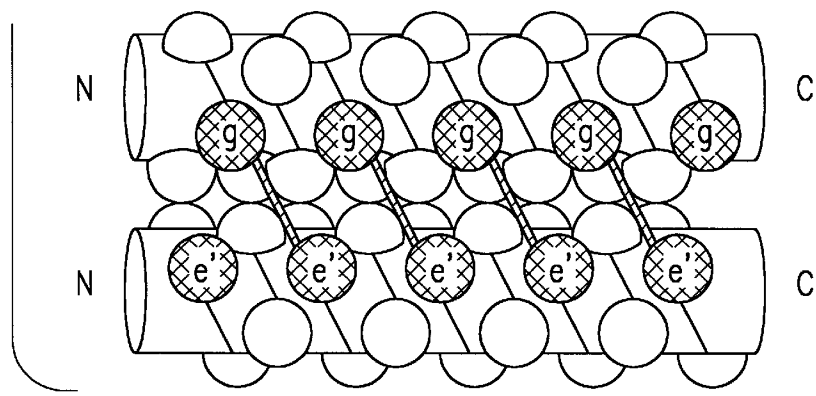
FIG. 1
APC-55 anti-APCp2
FIG. 2

PEPTIDE PROBES AND METHODS FOR MAKING THE SAME

This is a continuation-in-part of Provisional Patent Application No. 60/036,219, filed Jan. 28, 1997, in the name of the inventors listed above.

This invention was made with Government support under Grant No. RO1GM48958 awarded by the National Institutes of Health. The Government has certain rights to this invention.

FIELD OF THE INVENTION

The present invention relates generally to the field of biological probes, and more specifically to polypeptide probes directed to coiled coil proteins.

BACKGROUND OF THE INVENTION

Interactions among proteins are essential for the controlled function of all living cells, and inappropriate or adventitous protein-protein interactions are the hallmarks of virtually all diseases. Accordingly, biological probes directed at either the proteins themselves, or alternatively at their nucleic acid precursers, are essential for diagnosis of disease and general human health.

Existing biological probes are either nucleic acid-based or amino acid-based. Unfortunately, these prior art biological probes suffer from distinct and somewhat complementary disadvantages. Nucleic-acid based systems include oligonucleotides targeted for specific RNA or DNA sequences, which have the advantages of straightforward synthesis and simple rules for molecular complementarity. However, at present they can only be targeted easily to nucleic acids. Amino acid-based biological probes include antibodies, which can recognize a much broader range of molecules than nucleic acid-based probes. However, they are expensive and time-consuming to produce, requiring purification of the target and maintenance of animals. Moreover, functional antibodies cannot be expressed in intracellular compartments, and their use as biological probes often suffers from varying degrees of antigen expression, nonspecific binding and adverse immunogenic reactions.

Accordingly, there is a significant need in the art for a biological probe with broader applications than oligonucleotides and antibodies. Such a probe should combine the advantages of nucleic acid-based probes—quick synthesis, intracellular expression and easy labeling in vitro—with the specificity of antibodies for peptide sequences. Ideally, these probes should be sensitive, stable and recognize a wide range of biological molecules having different biological functions.

SUMMARY OF THE INVENTION

Accordingly, it is an object of the present invention to remedy the disadvantages encountered in prior art biological probes, through the provision of heterospecific polypeptide probes directed to coiled coil regions, and novel methods for making and using these probes.

In one embodiment, the present invention contemplates a polypeptide probe having a coiled coil region, wherein the core amino acid residues of the probe coiled coil region have been selected according to the core residue pairing rules so as to favor heterospecific oligomerization with a target coiled coil region. In a further embodiment, the amino acid residues of the probe coiled coil region are selected so as to optimize electrostatic interactions in the edge region of the interhelical interface adjacent to the core. In a specific embodiment, the probe comprises a substantially purified polypeptide sequence (SEQ ID NO: 2) directed to the APC protein. In a further embodiment, the invention comprises an isolated polynucleotide sequence encoding the polypeptide of SEQ ID NO: 2.

In an alternative embodiment, the present invention comprises a coiled coil structure formed between a target coiled coil region and a probe coiled coil region, wherein the amino acid residues located at positions a' and d' in the heptads of the probe coiled coil region are selected according to the core residue pairing rules. In a preferred embodiment, a leucine located at position a in a heptad of the target coiled coil region is paired with a preferred amino acid in the a' position in a heptad of the probe coiled coil region, wherein the preferred amino acid is selected from the group comprising: phenylalanine, isoleucine, lysine, methionine, serine, threonine and valine. In a further embodiment, a leucine located at position d in a heptad of the target coiled coil region is paired with a preferred amino acid in the d' position in a heptad of the probe coiled coil region, wherein said preferred amino acid is selected from the group comprising tryptophan, valine, arginine, glutamine, phenylalanine, asparagine, methionine, isoleucine and alanine.

In another preferred embodiment, a valine located at position a in a heptad of the target coiled coil region is paired with a preferred amino acid in the a' position in a heptad of the probe coiled coil region, wherein the preferred amino acid is selected from the group comprising: alanine, isoleucine, leucine, glutamine and serine. In a further embodiment, a valine located at position d in a heptad of the target coiled coil region is paired with a preferred amino acid in the d' position in a heptad of the probe coiled coil region, wherein said preferred amino acid is selected from the group comprising tyrosine, alanine, leucine, methionine, glutamine and threonine.

In an alternative embodiment, the present invention provides a hetero-oligomer comprising a polypeptide probe and a polypeptide target, wherein the probe comprises a first core region and the target comprises a second core region, and wherein a leucine in an a position in the second core region is paired with a preferred amino acid in an a' position of the first core region, wherein the preferred amino acid in the a' position is selected from the group comprising phenylalanine, isoleucine, lysine, methionine, serine, threonine, and valine. In a further embodiment, a leucine in the d position of the second core region is paired with a preferred amino acid in the d' position of the first core region, wherein the preferred amino acid in the d' position is selected from the group comprising tryptophan, valine, arginine, glutamine, phenylalanine, asparagine, methionine, isoleucine and alanine.

In an alternative embodiment, the present invention provides a hetero-oligomer comprising a polypeptide probe and a polypeptide target, wherein the probe comprises a first core region and the target comprises a second core region, and wherein a valine in an a position in the second core region is paired with a preferred amino acid in an a' position of the first core region, wherein the preferred amino acid in the a' position is selected from the group comprising alanine, isoleucine, leucine, glutamine and serine. In a further embodiment, a valine in the d position of the second core region is paired with a preferred amino acid in the d' position of the first core region, wherein the preferred amino acid in the d' position is selected from the group comprising tyrosine, alanine, leucine, methionine, glutamine and threonine.

The present invention also provides a heterospecific polypeptide probe directed to a coiled coil region of a target polypeptide, wherein the melting temperature of the hetero-oligomer formed between the probe and the target at a fixed total protein concentration is higher than the melting temperature of a homo-oligomer formed by either the probe or the target. In a preferred embodiment, the melting temperature of the hetero-oligomer is at least 8° C. higher than the average melting temperature of the homo-oligomers. In an alternative embodiment, the dissociation constant (Kd) of the hetero-oligomer formed between the probe and the target is lower than the dissociation constant of a homo-oligomer formed by either the probe or the target. In a particularly preferred embodiment, the dissociation constant of the hetero-oligomer is equal to or lower than 10 nM.

One embodiment of the methods of the present invention provides a method for making a heterospecific polypeptide probe, comprising the steps of 1) providing a target polypeptide having a target coiled coil region; 2) determining the target polypeptide sequence of the target coiled coil region; and 3) generating a probe polypeptide having a probe coiled coil region, wherein the probe polypeptide sequence of the probe coiled coil region is selected so as to favor heterospecific oligomerization of the probe coiled coil region to the target coiled coil region In a preferred embodiment, the probe polypeptide sequence is selected so as to optimize core residue pairing in the interhelical interface between the target coiled coil region and the probe coiled coil region. In a particularly preferred embodiment, the invention contemplates the application of novel core residue pairing rules so as to favor heterospecific pairing between the probe coiled coil region and the target coiled coil region. In a further embodiment, the probe polypeptide sequence is also selected so as optimize electrostatic interactions in the edge region of the interhelical interface. In a specific embodiment, the target polypeptide sequence is APC polypeptide or a portion thereof, and the probe polypeptide sequence is the polypeptide of SEQ ID NO: 2 or a portion thereof.

In an alternative embodiment, the invention provides a method for making a heterospecific polypeptide probe, comprising the steps of 1) providing a target polypeptide having at least one target coiled coil region, wherein the target coiled coil region comprises a first core region, a first edge region, and a first exposed region; 2) determining the amino acid sequence of the target coiled coil region; 3) generating a probe polypeptide having a probe coiled coil region, wherein the probe coiled coil region comprises a second core region, a second edge region, and a second exposed region; and 4) selecting amino acids in the second core region so as to optimize the formation of a heterospecific oligomer between the probe polypeptide and the target polypeptide. In a preferred embodiment, the method further comprises the additional step of selecting charged amino acids for the second edge region, wherein the charge on the charged amino acids in the second edge region is the same and is different from the charge on amino acids in the first edge region. In a particularly preferred embodiment, the method also comprises the additional step of selecting amino acids for the second exposed region so as to stabilize the probe coiled coil region.

Another alternative embodiment provides a method for making a heterospecific probe polypeptide sequence, comprising the steps of 1) providing a target polypeptide sequence having a first coiled coil region, wherein the first coiled coil region comprises at least three heptad sequences, with the heptad sequences containing amino acids at positions A, B, C, D, E, F, and G; 2) identifying the amino acids at positions A and D of the first coiled coil region; 3) generating a probe polypeptide sequence having a second coiled coil region, wherein the second coiled coil region comprises at least three heptad sequences, with the heptad sequences containing amino acids at positions A', B', C', D', E', F', and G'; and 4) selecting the amino acids at positions A' and D' such that the probe polypeptide sequence favors hetero-oligomerization with the target polypeptide sequence. In a further embodiment, the method comprises the additional steps of 5) identifying the amino acids at the positions E and G; and 6) selecting the amino acids at the positions E' and G' such that the probe polypeptide favors hetero-oligomerization with the target polypeptide sequence. In a specific embodiment, the amino acids at positions A' and D' are hydrophobic, and the amino acids at positions E' and G' are charged amino acids. In a still further embodiment, the charge on the amino acids at the positions E' and G' is the same and is different from the charge on the amino acids at the positions E and G.

The present invention also contemplates a method for detecting a coiled coil protein, comprising the steps of 1) providing: a) a target polypeptide sequence having a first coiled coil region; and b) a probe polypeptide sequence having a second coiled coil region; 2) combining the target polypeptide sequence with the probe polypeptide sequence such that a hetero-oligomer is preferentially formed between the target polypeptide sequence and the probe polypeptide sequence; and 3) detecting the hetero-oligomer. In an alternative embodiment, the present invention provides a method for detecting a target polypeptide sequence having a first coiled coil region in a sample, comprising the steps of: 1) providing: a) a sample suspected of containing a first polypeptide sequence; b) a second polypeptide sequence having a second coiled coil region; 2) combining the first polypeptide sequence with the second polypeptide sequence such that a hetero-oligomer is formed between the first polypeptide sequence and the second polypeptide sequence; and 3) detecting the hetero-oligomer.

BRIEF DESCRIPTION OF THE FIGURES

FIG. 1 shows the core (a and d) and edge (e-to-g) interactions in coiled coils.

FIG. 2 shows a helical wheel diagram of the APC-55 peptide and the designed anti-APCp2 polypeptide probe.

DEFINITIONS

Figure 3:
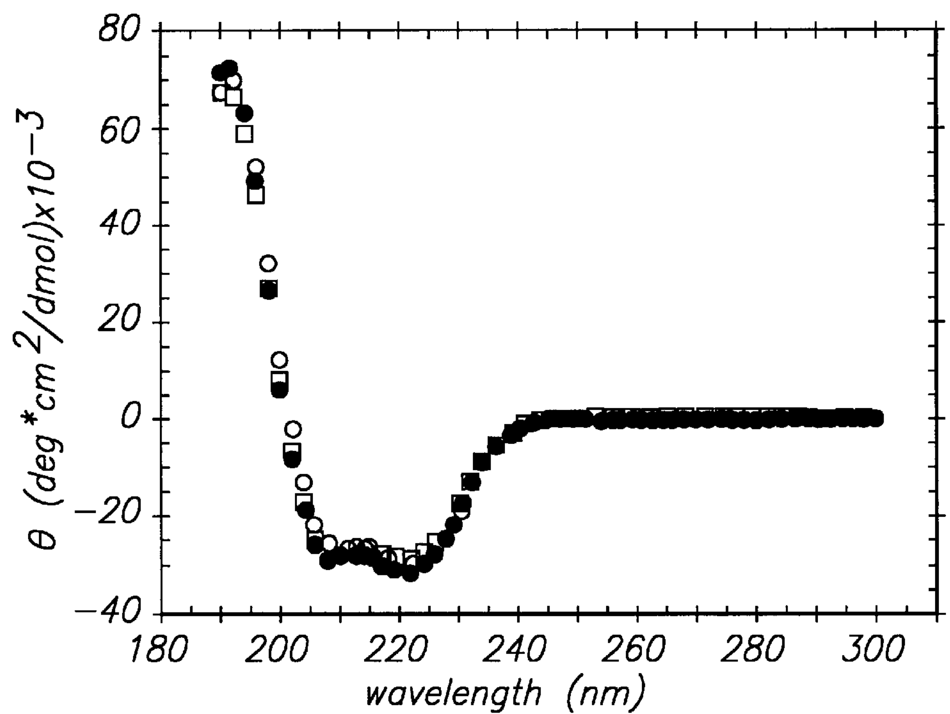
FIG. 3 shows the circular dichroism spectra of APC and anti-APC polypeptides.

To facilitate understanding of the invention, a number of terms are defined below.

The term "heptad" refers to a seven amino acid sequence in which the seven amino acids occupy the positions a, b, c, d, e, f, and g. In a given heptad, the amino acid at position a is located at the amino-terminal end, whereas the amino acid at position g is located at the carboxy-terminal end of the heptad.

The term "coiled coil region" refers to a polypeptide sequence containing two or more repeated heptads, i.e., $(a\ b\ c\ d\ e\ f\ g)_n$, where the a and d positions are generally, but not exclusively, occupied by hydrophobic residues; the b, c, e, f and g positions are generally, but not exclusively, occupied by hydrophilic residues; and n is a number equal to or greater than 2. A first "coiled coil region" which is placed in apposition with a second coiled coil region, with which it is capable of forming non-covalent bonds, generally adopts a secondary α-helical structure referred to as a "coil structure," as well as a tertiary left-handed superhelical structure referred to interchangeably as a "coiled coil structure" and a "supercoil structure." See, e.g., Lupas, "ITIBS 21:375–82 (1996). The distance that the superhelix requires to complete a full turn is called the "pitch," and the angle that each helix assumes relative to the superhelix axis is called the "superhelix crossing angle." The angle between two neighboring helices is called the "helix-crossing angle." There can be two or more (e.g., three, four or five) helices wound together in the superhelix and they can run either in the same ("parallel") or in opposite ("antiparallel") directions.

The term "coiled coil polypeptide" refers to a coiled coil structure comprising two or more polypeptides which in turn comprise one or more coiled coil regions. The polypeptides which comprise a coiled coil polypeptide may have the same or different amino acid sequences. Coiled coil polypeptides containing polypeptides of the same amino acid sequence generally have distinct coiled coil regions with intervening helix-breaking amino acid residues, which allow for protein folding and the oligomerization of succeeding coiled coil regions. For example, the seryl-tRNA-synthetase enzyme comprises an anti-parallel, dimeric coiled coil polypeptide with the two helices joined by a tight turn.

The "interhelical interface" denotes the region on each respective coiled coil region which non-covalently interacts with a neighboring coiled coil region to form a coiled coil. As is known in the art, the interhelical interface comprises the "hydrophobic core region" (which is also referred to as the "core region") and the "edge region." The "core region" is comprised of the amino acid residues located at positions a and d in the repeating heptad sequence (the "core residues"), while the "edge region" which is immediately adjacent to the core region, is comprised of the amino acid residues e and g of the heptad (the "edge residues"). The "exposed region," which faces away from a neighboring α-helix in the supercoil structure as illustrated in FIG. 1A, contains the amino acid residues located at positions b, c and f in the heptad (the "exposed residues").

The terms "oligomerization" or "oligomerize" as used herein in reference to polypeptide sequences refer to the non-covalent interaction between polypeptides.

The term "specific oligomerization," "specific binding," "specific pairing," "binding specificity," and "pairing specificity," when made in reference to two protein sequences is herein used to refer to the preferential oligomerization between two protein sequences as compared to the oligomerization between either of these two protein sequences to a third protein sequence. Specific oligomerization may be heterospecific or homospecific. The terms "homospecific oligomerization" and "homospecificity" as used herein refer to the specific oligomerization between two or more polypeptides having the same amino acid sequence. On the other hand, the terms "heterospecific oligomerization" and "heterospecificity" refer to the specific oligomerization between two or more polypeptides having different amino acid sequences. An amino acid sequence is different from another amino acid sequence if it contains one or more amino acids that are not the same as the amino acids in the other amino acid sequence.

The term "homospecific polypeptide" refers to a polypeptide sequence which preferentially oligomerizes with one or more other polypeptides having the same amino acid sequence as compared to oligomerization with one or more other polypeptides having a different amino acid sequence. In contrast, the term "heterospecific polypeptide" refers to a polypeptide which preferentially binds to other polypeptides of a different amino acid sequence when compared to oligomerization with other polypeptides that have the same amino acid sequence.

The terms "stable," "stable combination" and "stable association" when made in reference to two or more polypeptide sequences refer to the strength of the interaction between the polypeptides. The strength of interaction between polypeptides may be measured, for example, by the "dissociation constant" ($K_d$). The dissociation constant may be determined using methods known to one of ordinary skill in the art including, but not limited to, melting temperature ($T_m$) as measured, for example, by urea denaturation, competitive ELISA binding, etc.

The term "amino acid" as used herein refers to a hydrophobic, hydrophilic, charged, and/or uncharged amino acids as well as derivatives thereof. A "derivative" of an amino acid is a chemically modified amino acid. Illustrative of such modifications would be replacement of hydrogen by an alkyl, acyl, or amino group, or formation of covalent adducts with biotin or fluorescent groups. Such modifications may be desirable, for example, to bind or detect optically the polypeptide containing the derivative amino acid. Amino acids include biological amino acids as well as non-biological amino acids. The term "biological amino acid" refers to any one of the known 20 amino acids which a cell is capable of introducing into a polypeptide translated from an mRNA. The term "non-biological amino acid" refers to an amino acid which is not a biological amino acid. Non-biological amino acids are useful, for example, because of their stereochemistry or their chemical properties. The non-biological amino acid norleucine, for example, has a side chain similar in shape t that of methionine. However, because it lacks a side chain sulfur atom, norleucine is less susceptible to oxidation than methionine. Other examples of non-biological amino acids include aminobutyric acids, norvaline and allo-isoleucine, which contain hydrophobic side chains with different steric properties as compared to biological amino acids.

Hydrophobic amino acids are less soluble in water than hydrophilic amino acids. "Hydrophobic amino acids" include alanine, valine, leucine, isoleucine, proline, phenylalanine, tyrosine, tryptophan, methionine, aminobutyric acid, norvaline and allo-isoleucine. "Hydrophilic amino acids" include glycine, serine, threonine, tyrosine, asparagine, and glutamine. A "charged amino acid" is an amino acid which contains a net positive charge or a net negative charge. "Positively charged amino acids", which are also referred to as "basic amino acids," include lysine, arginine, and histidine. "Negatively charged amino acids," which are also referred to as "acidic amino acids," include aspartic acid and glutamic acid.

The term "derivative" when used in reference to a nucleic acid refers to the chemical modification of the nucleic acid. Illustrative of such modifications would be replacement of hydrogen by an alkyl, acyl, or amino group. A "derivative" when made in reference to a nucleic acid sequence refers to a nucleic acid sequence which contains one or more derivative nucleic acids. The term "derivative" as used herein in reference to a polypeptide sequence refers to a polypeptide sequence which contains one or more derivative amino acids.

The term "hetero-oligomer" when used in reference to polypeptides refers to a composition which contains two or more polypeptides, where the amino acid sequence of at least one polypeptide is different from the amino acid sequence of another polypeptide, and where the polypeptides interact via non-covalent bonds. A hetero-oligomer may be a heterodimer, heterotrimer, heterotetramer, etc. Heterodimers contain two polypeptides, heterotrimers contain three polypeptides, whereas heterotetramers contain four polypeptides.

The term "homo-oligomer" as used herein in reference to polypeptides refers to a composition which contains two or more polypeptides, where the amino acid sequence of each and every polypeptide is the same, and where the polypeptides interact non-covalently. A homo-oligomer may be a dimer, trimer, tetramer, etc.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

As used herein, the term "probe" when made in reference to an oligonucleotide (i.e., a sequence of nucleotides) refers to an oligonucleotide, whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. Oligonucleotide probes may be labelled with a "reporter molecule," so that the probe is detectable using a detection system. Detection systems include, but are not limited to, enzyme, fluorescent, radioactive, and luminescent systems.

The term "probe" when used in reference to a polypeptide refers to a polypeptide which is capable of interacting with another polypeptide of interest. Polypeptide probes may be produced synthetically or by recombinant means. Chemicals methods for polypeptide synthesis are known in the art, such as those described by Cartuthers et al., (1980) Nuc. Acids Res. Symp. Ser 215–23, and by Horn et al. (1980) Nuc. Acids Res. Symp. Ser 225–32. Alternatively, a polypeptide probe may be produced by expression in an expression vector of polynucleotides (i.e., a sequence of nucleotides) encoding the probe. Probes are useful in the detection, identification and isolation of particular polypeptide sequences. It is contemplated that the polypeptide probes of the invention may be, but are not necessarily, used in combination with a label. The polypeptide probes of the present invention may be labelled with any "reporter molecule," so that the polypeptide reporter is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The polypeptides of the present invention may also be used for the isolation of a polypeptide of interest. For example, the polypeptide probe may be fused to another molecule capable of binding to a ligand, and the polypeptide isolated by binding the fused composition to the ligand. The ligand may be immobilized to a solid support to facilitate isolation of the fused polypeptide. Ligand-binding systems useful for the isolation of polypeptides are commercially available and include, for example, the staphylococcal protein A and its derivative ZZ (which binds to human polyclonal IgG), histidine tails (which bind to $Ni^{2+}$), biotin (which binds to streptavidin), maltose-binding protein (MBP) (which binds to amylose), glutathione S-transferase (which binds to glutathione), etc. It is not intended that the polypeptide probes of the present invention be limited to any particular isolation system.

The term "sample" as used herein is used in its broadest sense and includes environmental and biological samples. Environmental samples include material from the environment such as soil and water. Biological samples may be animal or plant, including, human, fluid (e.g., blood, plasma and serum), solid (e.g., stool), tissue, liquid foods (e.g., milk), and solid foods (e.g., vegetables). A biological sample suspected of containing APC polypeptide may comprise a cell, tissue extract, body fluid, protein (in solution or bound to a solid support such as for Western blot analysis), and the like.

The terms "polypeptide of interest" refer to any polypeptide, the manipulation of which may be deemed desirable for any reason, by one of ordinary skill in the art.

The term "portion" when used in reference to a protein (as in a "portion of a given protein") refers to fragments of that protein. The fragments may range in size from four amino acid residues to the entire amino acid sequence minus one amino acid residue.

As used herein, "APC coiled coil probe" or "APC coiled coil polypeptide probe" refers to the amino acid sequence of a substantially purified polypeptide which comprises a coiled coil region, wherein the coiled coil region is capable of specific oligomerization with an adenomatous polyposis coli (APC) protein obtained from any species (particularly mammalian, and preferably human) from any source whether natural, synthetic, semi-synthetic or recombinant.

A "variant" when made in reference to a polypeptide sequence is defined as an amino acid sequence which differs by one or more amino acids from the polypeptide sequence.

The term "biologically active" when made in reference to a coiled coil polypeptide refers to a coiled coil polypeptide molecule which is capable of specific oligomerization with another coiled coil polypeptide molecule.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

"Amplification" is defined as the production of additional copies of a nucleic acid sequence and is generally carried out using polymerase chain reaction technologies well known in the art [Dieffenbach C W and G S Dveksler (1995) *PCR Primer, a Laboratory Manual*, Cold Spring Harbor Press, Plainview N.Y.]. The term "polymerase chain reaction" ("PCR") refers to the method of K. B. Mullis, U.S. Pat. Nos. 4,683,195 and 4,683,202, hereby incorporated by reference.

The term "hybridization" as used herein refers to any process by which a strand of nucleic acid joins with a complementary strand through base pairing.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support [e.g., a nylon membrane or a nitrocellulose filter as employed in Southern and Northern blotting, dot blotting or a glass slide as employed in in situ hybridization, including FISH (fluorescent in situ hybridization)].

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing." [Coombs J (1994) *Dictionary of Biotechnology*, Stockton Press, New York N.Y.].

"Stringency" when used in reference to nucleic acid hybridization typically occurs in a range from about $T_m$−5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" SEQ ID NO: 2 or fragments thereof will hybridize to its exact complement and closely related sequences. The stringent conditions are chosen such that SEQ ID NO: 2 or fragments thereof will hybridize to sequences encoding the APC polypeptide of SEQ ID NO: 1.

GENERAL DESCRIPTION OF THE INVENTION

The present invention solves the problems in the prior art through the provision of a polypeptide probe system directed specifically to the coiled coil region of a target protein. The coiled coil region is a widely-distributed protein motif containing a seven-residue repeat labelled $(a\ b\ c\ d\ e\ f\ g)_n$, with hydrophobic residues generally occurring at the a and d positions and largely polar residues elsewhere. This repeating heptad forms a right-handed α-helix, which is capable of wrapping around an opposing coiled coil region in a left-handed supercoil, provoking the name "coiled coil." As illustrated in FIG. 1, the a and d positions typically comprise the hydrophobic core of the interhelical interface, with the charged e and g residues on the edge of the interhelical interface adjacent to the core.

In order to provide an effective biological probe, the hetero-oligomer formed by the target and probe polypeptides should be more stable than either homo-oligomer. The methods described herein provide a polypeptide probe sequence with high affinity for any desired coiled coil region, effectively competing with the natural pairing. The invention contemplates selective amino acid pairing and packing in the hydrophobic core of the interhelical interface, as well as optimization of the electrostatic interactions in the amino acid residues surrounding the hydrophobic core.

Thus, the methods of the present invention can be used to provide heterospecific polypeptide probes based solely on the amino acid sequence of the target protein. Since coiled coil regions can be found in a multitude of important proteins, including, but not limited to, cytoskeletal components, transcriptional activators, tumor suppressors, components of the mitotic apparatus, nuclear envelope proteins, extracellular matrix components, oncogene products, muscle proteins, cell and viral surface proteins and molecular motors, it is contemplated that the polypeptide probes of the present invention will have broad diagnostic and therapeutic application.

I. Coiled Coil Proteins

The coiled coil has a distinguished history. In 1952, Crick and Pauling raced to propose the coiled-coil structure to reconcile Pauling's model of the α-helix with the diffraction patterns of a variety of fibrous proteins, including keratin. Crick, *Nature* 170:882–83 (1952); Pauling and Corey, *Nature* 171:59–61 (1953). Importantly, in 1953 Crick proposed a detailed mathematical model of the coiled coil family in which the characteristics of the supercoil (radius, pitch, helix crossing angle, etc.) were shown to be dependent on each other. Crick, *Acta Cryst.* 6:685–89 (1953). Crick also described a physical model (based on the packing of nails hammered into a broom handle) for the packing of hydrophobic side chains in the interface between the helices. Crick, *Acta Cryst.* 6:689–97 (1953). The essence of this model, which Crick termed "knobs-into-holes" packing, was that each core side chain (the knob) would fit in the space (the hole) between four side chains in the neighboring helix. This packing model is considered to be the hallmark of a true coiled coil structure. See, e.g., Lupas, ITIBS21:375–82 (1996).

As noted above, the sequences of coiled coil proteins revealed a common seven-residue repeat, $(a\ b\ c\ d\ e\ f\ g)_n$, with the first (i.e., a) and fourth (i.e., d) positions generally occupied by hydrophobic residues. The occurrence of hydrophobic residues spaced every three and then four residues apart is a characteristic of all coiled coil sequences, and the sequence is strongly maintained for structural reasons. The seven helical residues sweep out 700°, 20° short of two full turns. As a result, succeeding hydrophobic residues wind gently around the helix, and the coiled coil forms when the hydrophobic stripes associate. The coiled coil family now includes seven structural classes—dimers, trimers, tetramers with parallel or antiparallel helices, as well as a pentamer with parallel helices. See Wagner and Green, *Science* 262:395–99 (1993); (Table 1).

The number of proteins found to contain coiled-coil motifs has grown in equal measure to the sequence data base. Cohen and Parry, *Proteins* 7:1–15 (1990). Coiled-coil proteins include the transcription factors and oncogene products in the bZIP and bHLH-ZIP families, as well as tumor suppressors, such as APC. Longer coiled coils occur in structural proteins of the cytoskeleton, nuclear matrix, mitotic spindle, molecular motors, muscle, extracellular matrix and surface proteins of cells and viruses, and the methods and probes of the present invention can be used to detect these target coiled coil proteins either in vitro or in vivo, or alternatively to differentiate the tissue and/or the cells expressing the target protein when it is expressed exclusively by that tissue and/or cell type. In addition to providing oligomerization domains and spacers, coiled coils are bound by other proteins (Wagner (1993). The following Table provides an illustrative example of the rich variety of coiled coil proteins which can be analyzed and manipulated using the methods and probes provided by the present invention.

TABLE 1

COILED COIL PROTEINS

| | Number of α-helices | | | |
|---|---|---|---|---|
| Orientation | TWO | THREE | FOUR | FIVE |
| PARALLEL | Leucine zipper<br>APC<br>myosins<br>tropomyosins<br>Intermediate Filament proteins | Hemagglutinin<br>Heat Shock Factor<br>Laminin<br>Fibrinogen<br>Phage T7 leg<br>Tenascin | GCN4-pLI | Cartilage Oligomer Matrix Protein |
| ANTI-PARALLEL | Seryl tRNA synthetase<br>Serum Response Factor | Spectrin<br>Coil-Ser | Repressor of Primer<br>LacI | |

Published reports in the literature describing specific examples of coiled coil proteins include Wilson et al., *Nature* 289:366 (1981) (hemagglutinin); Banner et al., *J. Mol. Biol.* 196:657–75 (1987); O'Shea et al., *Science* 254:539–44 (1991); Cohen & Parry, supra; Cusack et al., *Nature* 347:249–55 (1990) (seryl-tRNA synthetase); Beck et al., *J. Mol. Biol.* 231:311–23 (1993) (laminin); Lovejoy et al., *Science* 259:1288–93 (1993); Yan et al., *Science* 262:2027–30 (1993) (spectrins); Holberton et al., *J. Mol. Biol.,* 204:789–95 (1988) (giardin); Koski et al., *J. Biol. Chem.,* 267:12258–65 (1992) (the protein TlpA from *Salmonella typhimurium*); Ayer et al., *Cell* 72:211–22 (1993) (Myc oncoprotein Max); Gauger & Goldstein, *J. Biol. Chem* 268:13657–66 (1993) (Drosophilia kinesin light chain); Marshal & Holberton, *J. Mol. Biol.* 231:521–530 (1993); and Zervos et al., *Cell* 72:223–32 (1993) (Mxi1). In addition, coiled coil databases have been constructed and analyzed to verify the existence of coiled coil regions in a multitude of proteins. See, e.g., Woolfson and Alber, *Protein Science* 4:1596–1607 (1995); Berger et al., *Proc. Natl. Acad. Sci. USA* 92:8259–63 (1995).

The methods of this invention contemplate the use of coiled coil polypeptides which are capable of hetero-oligomerization with any desirable target polypeptide which contains a heptad repeat. The methods of this invention are not limited to the number of polypeptides in the target coiled coil polypeptide. For example, the target coiled coil polypeptides may comprise two, three, four, five, or more polypeptides (see, e.g., Table 1). Examples of coiled coil proteins which contain two polypeptides include the β-isoform of human cardiac, heavy-chain myosin; human tropomyosin, α and γ chains; paramyosin; human desmoplakins I and II; the transcriptional activator, GCN4; human cytokeratins 1 and 10; and the N-terminal 80 amino acids of the human adenomatous polyposis coli (APC) protein, etc. Examples of coiled coil polypeptides which comprise three polypeptides include human laminins A, B1 and B2; the B chain of influenza hemagglutinin; the trimerization region of the human heat shock transcription factor, hsf2; human fibrinogen, β and γ chains; the human macrophage scavenger receptor; the DNA packaging protein, GP17; human tenascin; the whisker antigen control protein, fibritin, etc.

The invention further contemplates coiled coil proteins comprising the same or different amino acid sequences. Also expressly included within the invention's scope are coiled coil polypeptides in which the α-helices run in the same (parallel) or in opposite (antiparallel) directions.

Also contemplated within the scope of this invention are coiled coiled regions which contain discontinuities in the heptad repeat, including, but not limited to, non-helical regions, skip residues, and omission of either three or four residues from the heptad repeat. "Non-helical regions" are amino acid sequences which do not contain a heptad repeat, and they generally give the coiled coil region in which they are located the appearance of a segmented rope. A "skip residue" refers to a coiled coil region in which one or more heptad repeats contains one or more extra amino acid residues (e.g. abcdeffg). The skip residue structures are observed, for example, in the 'thumb' of DNA polymerase 1 (PolI). "Omissions of three residues" and "stutters" refer to the absence of three amino acid residues from the heptad repeat. These cause a local decrease in the extent of supercoiling as they correspond to slightly less than a full turn of the helix. Stutters shift residues in position a towards the center of the core region, resulting in a geometry called an x layer (i.e., abcdefgxelg). "Omissions of four residues" refers to the absence of four amino acid residues from the heptad repeat. These cause an increase in supercoiling as they correspond to slightly more than a helix turn. Their effect is to shift residues in a into a da layer (abcedfgelg) and residues in d into an x layer (i.e., abcxbcdelg).

II. Specificity of Coiled Coil Binding

Despite having a common structure, the hundreds of coiled coil motifs within a cell generally exhibit specific binding preferences. Thus, while sharing a common structure, dimeric coiled coils pair specifically. O'Shea, *Cell* 68, 699–708 (1992). This specificity has been demonstrated in wild-type protein sequences (Lavigne, et al., *J. Mol. Biol.* 254, 505–20 (1995); Kammerer et al., J. Engel, *J. Mol. Biol.* 250, 64–73 (1995); O'Shea, *Science* 245, 646–8 (1989)) and synthetic model systems (Graddis et al., *Biochemistry* 32, 12664–71 (1993); Hodges et al., *J. Biol. Chem.* 256, 1214–1224 (1981); Nautiyal et al., *Biochemistry* 34, 11646–11651 (1995).

A clear example of this specificity is afforded by the oncogene products Fos and Jun, whose leucine zippers (a classic coiled coil sequence having a leucine every seven residues) have been found to mediate preferential pairing with each other to form a heterodimer. See, e.g. O'Shea et al. (1989); O'Shea et al. (1991); Alber, *Curr. Opin. Genet. Dev.* 2:205–10 (1992). Subsequent experiments with the Fos-Jun model demonstrated that the e and g positions of the coiled coil heptad were determinative of this specificity, since repulsive ionic interactions between the e and g residues of Fos were relieved by complementary charges in the heterodimer. O'Shea et al. (1992). Importantly, these investigators also found that substitution of the a and d residues in the hydrophobic core did little to alter the preference for heterodimer formation. See, e.g., FIG. 5 of O'Shea et al. (1992) supra. Based on these studies, the investigators concluded that the major thermodynamic driving force for preferential heterodimer formation was the destabilizing electrostatic interactions at the e and g positions in the edge region adjacent to the hydrophobic core.

This analogous charge complementation at the e and g positions has formed the basis for the design of synthetic heterodimers, and for peptides that bind to specific leucine zipper targets. See, e.g., O'Shea et al., *Current Biol.* 3(10):658–67 (1993); Zhou et al., *J. Mol. Biol.* 237:500–12 (1994); Krylov et al., *EMBO J.* 13:2849–61 (1994). In contrast to modifications of the e and g residues, prior art attempts to design heterodimeric coiled coils with alternative core residue packing in the interhelical interface did not result in heterodimers that were more stable than the corresponding homodimers. See Zhu et al., *Int. J. Pept Protein Res.* 40:171–79 (1992). Thus, the prior art has focused almost exclusively on optimizing the electrostatic interactions at the e and g positions of the coiled coil heptad in order to drive oligomer heterospecificity.

In contrast, the methods of the present invention focus in significant part on optimal amino acid residue pairing in the core region of the interhelical interface. To date, these interactions have been far less well understood. See Lupas, *TIBS* 21, 377 (1996). However, the preferred embodiments of the methods of the present invention provide a solution to this persistent problem in the art, through the provision of core residue pairing rules which optimize the packing and polarity of the core amino acids located at the a and d positions in the heptad. In addition, a further embodiment of the present invention also incorporates the optimization of the electrostatic interactions in the edge regions of opposing helices, to further enhance the heterospecificity of the polypeptide.

To develop pairing rules that could guide the design of antisense coiled-coil peptides, we relied on thermodynamic measurements of specificity ((O'Shea (1992); Vinson et al., *Genes Dev.* 7, 1047–58 (1993).; Krylov et al., *EMBO J.* 13, 2849–2861 (1994)) and covariation frequencies in coiled-coil sequences (FIG. 1). In both natural and model coiled coils, specific associations have been attributed to destabilizing ionic interactions in the homodimers that are replaced with more favorable contacts in the heterodimer (O'Shea (1992); Vinson et al. (1993).; Krylov et al. (1994); Zhou et al., *Prot. Eng.* 7, 1365–1372 (1994)). Consequently, our anti-APC design included charged amino acids at g and succeeding e' positions that could form ion pairs in the heterodimer and repulsive ionic interactions in the antisense peptide (Vinson (1993)).

In contrast to the g and l positions, little specificity has been ascribed to core residue contacts (O'Shea (1992); Lavigne (1995), Lumb et al., *Biochemistry* 34, 8642–8 (1995); Zeng et al., *Proc. Narl. Acad. Sci. USA* 94, 3673–3678 (1997)). In the heterodimer formed by the Fos and Jun leucine zippers, for example, three heterotypic pairs of core residues appear to impart none of the observed preference of the chains for each other (O'Shea (1992)). This is surprising, considering that the core residues form the majority of interhelical contacts (O'Shea (1991), and mutations of core residues have dramatic effects on stability and oligomerization (Monera et al., *Prot. Eng.* 9, 353–63 (1996); Harbury et al., *Science* 262, 1401–7 (1993); Harbury et al., *Nature* 371, 80–83 (1994); Lovejoy et al., *Science* 259, 1288–93 (1993); Vieth et al., *J. Mol. Biol.* 251, 448–67 (1995); Zhu et al., *Prot. Sci.* 2, 383–94 (1993)).

To obtain rules for core complementation, we analyzed the sequences of the coiled-coil domains in cytokeratins that form obligate heterodimers (Corden et al., *Exp. Dermatol.* 5, 297–301 (1996); Steinert et al. *Ann Rev. Cell Biol.* 1, 41–65 (1985)). Four pairs (comprising four known keratin sequences) were used in the analysis. Sequences are available in the Swissprot database with the following accession numbers: K8 (P05787), K18 (P05783), K4 (P19013), K13 (P13646), K5 (P13647), K14 (P02533), K1 (P04264), and K10 (P13645). Uneven frequencies of heterotypic and homotypic pairing provided evidence for core mediated specificity and revealed the identities of preferred interhelical neighbors.

III. Applications of the Present Invention

Because coiled coils are central to many areas of biology, the new technology provided by the present invention has a variety of advantageous uses. These include, for example, staining target proteins on gels and in cells, inactivating coiled coils in vivo, affinity purification of a target protein as well as coprecipitation and identification of any associated proteins, tagging cells for sorting, disassembling viruses, screening tissue for mutant forms of a protein, developing drugs that block oligomerization, and diagnosing human diseases such as colon cancer. Fusion to sequences that target proteins for degradation also ultimately will allow peptide probes to reduce the level of specific target proteins in vivo.

Additional applications for peptide probe technology are also contemplated. Probes against any coiled coil proteins may be designed using this approach, and used to detect target coiled coil proteins or alternatively to differentiate tissue and/or cells expressing a tissue- or cell-specific target protein from surrounding tissue, such as for example in histological staining. Moreover, the probes may prove suitable for expression alone or as fusion proteins within cells, because unlike antibodies, the peptide probes do not require disulfide bonds for structural stability. Also unlike antibodies, which can recognize the native structure of their target, peptide probes for coiled coils necessarily disrupt the structure of the target coiled coil. As a result, the peptide probe can unfold and inactivate the target. This property is useful in applications in research and medicine.

DETAILED DESCRIPTION OF THE PREFERRED EMBODIMENTS

As noted above, the methods of the present invention contemplate the creation of a heterospecific polypeptide probe, by focusing on both packing and preferential pairing in the hydrophobic core between the opposing helices, and on optimizing electrostatic interactions in the edge region adjacent to the core.

I. Sequence Alterations Contributing to Heterospecificity

A. The Core Residue Packing Rules

The methods and probes of the present invention contemplate the incorporation of core residues into the probe polypeptide to conserve packing volume and, in a preferred embodiment, to duplicate a–a' and d–d' pairs that occur with enhanced frequency in the sequences of obligate heterodimeric coiled coils. In the preferred embodiment, the sequences of suitable obligate heterodimers are analyzed in accordance with the disclosed method to identify preferred heteromeric pairs of amino acids. Once the sequence of the target coiled coil region has been determined, these pairing preferences are used to identify and incorporate the optimal amino acid into the opposing position in the core region of the probe polypeptide. Thus, the pairing preferences provided by the present invention provide an initial set of imperical rules for complementation in the core of the interhelical interface between opposing coiled coil regions.

In a particularly preferred embodiment, the polypeptide probes of the present invention are constructed in accordance with the pairing frequencies found in keratin heterodimers. In keratins, small residues in the core region of one helix are generally paired with larger side chains in the core of the opposing helix. In addition, polar residues in the interhelical interface are generally paired with polar residues in the opposing interface. These general principles, along with the preferred heteromeric pairs derived from analysis of the keratin sequences, are employed in the preferred embodiments of the methods of the present invention to create a heterospecific polypeptide probe directed to any target coiled coil region.

B. Optimizing Electrostatic Interactions in the Edge Region

The methods and probes of the present invention also contemplate the optimization of electrostatic interactions in the edge region of the coiled coil, as disclosed to some extent in the prior art. Thus, the polypeptide probes of the present invention preferably also incorporate repulsive charge/charge interactions at position g and position e of the succeeding heptad to disfavor homo-oligomerization of the polypeptide probe, as well as complementary charges in comparison with the opposing edge region in the target polypeptide in order to aid in favorable interhelical ionic interactions in the hetero-oligomer.

II. Sequence Alterations Not Contributing to Heterospecificity

The present invention further contemplates that additional advantageous sequence alterations can be made in the probe polynucleotide sequence which are not considered to influence heterospecific oligomerization. For example, several alterations can be made at the (f) position in the heptad in order to 1) change the overall charge of the probe in order to facilitate experimental analysis of pairing; 2) preserve the overall stability of the system by incorporating a residue with significant helical propensity, such as Lysine or Alanine; 3) promote the solubility of the probe peptide; and 4) introduce chromogenic groups (e.g Tyrosine) to allow the probe to be detected optically. Other and further advantageous alterations, known to those of skill in the art, can be employed where appropriate to the specific target protein and/or application contemplated for a given probe polypeptide.

III. Generation of a Coiled Coil Polypeptide

Coiled coil polypeptides may be made using any of several methods known in the art including synthetic and recombinant methods. Chemicals methods for polypeptide synthesis are known in the art, such as those described by Caruthers et al., (1980) Nuc. Acids Res. Symp. Ser 215–23, and by Horn et al., (1980) Nuc. Acids Res. Symp. Ser 225–32. Automated chemical protein synthesis is routine in the art, for example using "Fast Moc" chemistry on an Applied Biosystems model 431A peptide synthesizer. Briefly, amidated peptide may be prepared using Rink resin (Advanced Chem Tech), whereas peptide containing free C termini may be synthesized on Wang (p-alkoxybenzyl alcohol) resin (Bachem). First, residues are double coupled to the appropriate resin and subsequent residues are single coupled. Each coupling step is followed by acetic anhydride capping. Peptide are cleaved from the resin by treatment with trifluoroacetic acid (10 ml), water (0.5 ml), thioanisole (0.5 ml), ethanedithiol (0.25 ml) and crystalline phenol (0.75 ml). Purification may be carried out by reverse-phase HPLC. Samples of crude peptide may be chromatographed on a Waters Delta Pak C18 column with a linear gradient as described by Cionciolo, et al. (1988) *Immunol. Lett.* 19:7–14. Lyophilized peptide may be stored either desiccated or in an aqueous solution. Electrospray mass spectrometry may be used to confirm the purity and size of the synthesized coiled coil polypeptide.

Alternatively, a coiled coil polypeptide may be produced by expression in an expression vector of polynucleotides (i.e., a sequence of nucleotides) encoding the coiled coil polypeptide. For example, the nucleic acid sequence encoding the coiled coil polypeptide may be expressed either alone or as a fusion polypeptide ligated to one or more heterologous sequences as part of a fusion gene. Fusion genes may be desirable, for example, for the detection or the purification of the coiled coil protein. Examples of a heterologous sequence useful for the detection of the expression of the coiled coil polypeptide include the reporter sequence encoding the enzyme β-galactosidase or the enzyme luciferase. Fusion genes desirable to facilitate purification of the expressed coiled coil polypeptide include the protein A which allows purification of the fusion protein on immobilized immunoglobulin. Other affinity traps are well known in the art and can be utilized to advantage in purifying the expressed fusion protein. For example, pGEX vectors (Promega, Madison Wis.) may be used to express the coiled coil polypeptide as a fusion protein with glutathione S-transferase (GST). In general, such fusion proteins are soluble and can easily be purified from lysed cells by adsorption to glutathione-agarose beads followed by elution in the presence of free glutathione. Other fusion polypeptides useful in the purification of the coiled coil polypeptide are commercially avaible, including histidine tails (which bind to $Ni^{2+}$), biotin (which binds to streptavidin), and maltose-binding protein (MBP) (which binds to amylose). It is not intended that the coiled coil polypeptides of the present invention be limited to any particular isolation system. Coiled coil polypeptides made in such systems are designed to include heparin, thrombin or factor XA protease cleavage sites so that the cloned polypeptide of interest can be released at will from the heterologous polypeptide moiety to which it is fused.

IV. Methods for Verifying Heterospecificity and Stability in the Probe Polypeptide Coiled coil polypeptides are useful in the detection, identification and isolation of particular polypeptide sequences, and in detecting and differentiating the cells and/or tissues which express these proteins. These uses are feasible as a result, in part, of the heterospecificity of the coiled coil polypeptides for other polypeptides containing coiled coil regions, and the stability of the formed hetero-oligomers. The ability of the methods of the present invention to create a stable, heterospecific polypeptide probe can be easily demonstrated using standard biochemical techniques known to those of skill in the art. As an initial approach, heterospecificity of a coiled coil polypeptide is determined prior to the quantitation of heterospecificity. Heterospecificity is determined using a number of methods known in the art, including, but not limited to, circular dichroism, thermal denaturation, equilibrium centrifugation, direct measurement of dissociation constants, disulfide exchange measurements, ion exchange chromatography, western blot analysis, precipitation of target proteins, biological screening methods, and native gel electrophoresis.

Circular dischroism investigations are well known in the art. For example, such an investigation may be performed using a 1 cm or 1 mm cuvette (Helma or Uvonic) on an Aviv CD spectrophotometer (model 60DS or model 62DS) equipped with a thermoelectric controller. The buffer used for all CD experiments except pH titrations is 100 mM KF, 10 mM potassium phosphate (pH 7.0). All peptide concentrations may be determined by tyrosine absorbance at 275.5 nm in 6.0 M GuHCl PH 6.5 (Schwarz/Mann Biotech Ultra-Pure grade) using an Aviv UV/VIS spectrophotometer (model 1 BDS or 14 DS). The molar ellipticity at 222 nm, 5° C., is measured for the homo- and heterodimers. The CD values (i.e., deg $cm^2$ and $dmol^{-1}$) indicate % helicity of the peptides. Thermal melting curves are determined by monitoring the CD signal at 222 nm as a function of temperature. The pH dependence of stability may be measured in 100 mM KF, 10 mM potassium phosphate at various pH values. GuHCl (Schwarz/Mann Biotech Ultra-Pure grade) (e.g., 2M) may be included in the buffer used for monitoring the pH dependence of stability. pH stability is indicated if the same overall shape of the pH dependence curve is obtained in the absence as well as the presence of GuHCl. It is also desirable to determine the reversibility for all thermal melts. The absence of reversibility of a melting curve above a certain pH value indicates chemical modification and/or degradation of the polypeptide. Such modification and/or degradation may be confirmed using HPLC.

Thermal denaturation is used to determine $T_m$. The term "$T_m$" refers to the temperature at which the fraction of a polypeptide which is unfolded is equal to the fraction folded ($\Delta G=0$). The $T_m$ is determined by curve fitting a thermal denaturation curve (described supra) to an equation known in the art (see, O'Shea et al (1992) Cell 68:699–708) using a nonlinear least squares-fitting program (e.g., Kaledagraph, Synergy Software). Alternatively, the $T_m$ for each polypeptide may also be determined by taking the first derivative of the CD signal (β) with respect to $temperature^{-1}$ (temperature in K) and finding the minimum of this function (Cantor and Schimmel, 1980). Similarly, denaturation induced by additives such as urea or GuHCl can be followed by circular dichroism. These measurements can yield the $C_m$, i.e., the denaturant concentration where ΔG=0. Linear extrapolation of the transition to zero denaturant can yield the equilibrium constant in aqueous buffer. This can be converted to a free energy of association using the formula ΔG=—RTlnK [Cantor and Schimmel (1980) supra).

Equilibrium centrifugation is yet another routinely used alternative method for the determination of the specificity of hetero-oligomerization. Briefly, this method involves ultracentrifugation of different concentrations of each peptide alone and in combination, analyzing samples for the presence of protein (e.g., by measuring absorbance at 280 nm), and determination of partial specific volumes based on the amino acid compositions of the peptide and apparent molecular weights using commercially available software.

Direct measurement of dissociation constants (Kd's) may also be used to determine the specificity of polypeptide hetero-oligomerization and may be accomplished using any number of quantitative binding methods. These methods include, but are not limited to, fluorescence, plasmon resonance, gel shifts, competition ELISA and mass spectrometry.

Disulfide exchange measurements are also routinely used in the art to determine the specificity of polypeptide hetero-oligomerization. Polypeptide variants capable of forming a disulfide bond in the folded structures of all possible peptide combinations are mixed in a redox buffer. The redox buffer, consisting for example of a mixture of reduced and oxidized glutathione, allows assortment of the disulfide bonded species. After equilibrium is reached, the disulfide exchange is quenched at low pH and the ratio of oxidized species is determined. Deviations from the expected 1:2:1 binomial distribution quantitatively indicate specificity if the heterodimer is enriched and anti-specificity if the homodimers are enriched. E. K. O'Shea, R. Rutkowski, W. F. Stafford III and P. S. Kim (1989), *Science,* 245: 646–648.

Yet another method for the determination of hetero-oligomerization specificity is ion exchange chromatography which is capable of resolving polypeptide species with different charges (Nautiyal et al. (1995). A further method for determining the specificity of hetero-oligomerization is by using the coiled coil polypeptide probe whose specificity is sought to be determined to bind to Western blots f cell lysates or other mixtures of proteins. Exclusive binding to a target protein indicates a preference or specificity for the target.

Additionally, precipitation of target proteins may be used to determine the hetero-oligomerization specificity of a coiled coil polypeptide probe to the target proteins. Coupling the probe polypeptide to biotin, GST, His tag or other epitope allows probe-bound complexes to be rapidly removed from cell lysates. Analysis of the targets bound to the probe by SDS gel electrophoresis and Western blotting allows the preference for the target protein to be assessed.

Other biological screening methods, such as phage display of the "two-hybrid" system may also be used to determine the hetero-oligomerization specificity of a coiled coil polypeptide. Expression of the probe sequence (or a portion thereof) on the surface of a filamentous phage might allow specificity to be estimated by panning the phage population using the target polypeptide. Alternatively, specificity might be detected in vivo by attaching the coiled coil target polypeptide and the coiled coil probe polypeptide to the GAL4 DNA binding domain and the activation domain in a two hybrid reporter system in yeast. Preferential binding of the probe to the target could lead to increased expression of the reporter gene.

Native gel electrophoresis is the preferred method for the determination of specificity of hetero-oligomerization. In this method, the individual peptides and an equimolar mixture of the peptides are electrophoresed on gels in the absence of denaturing compounds (e.g., urea, SDS, etc.) and the location of the polypeptide bands determined using for example, Coomassie Brilliant Blue. The formation of a band of a different mobility when the two polypeptides are combined and the absence of the bands corresponding to the individual polypeptides indicates heterospecificity.

In addition to the determination of whether or not a coiled coil polypeptide exhibits heterospecificity, the degree of specificity of a coiled coil polypeptide (e.g., a probe) for another coiled coil polypeptide (e.g., a target) can be quantitated using methods known in the art, such as those described by O'Shea et al. (1993) Current Biology 3:658–667. Briefly, specificity may be estimated using the equilibrium constant $K_{spec}$ which describes the ratio of heterodimers to homodimers, and which can be expressed in terms of the dissociation constants for each dimer. Assuming a two-state model for monomer-dimer equilibrium, then $$K_{spec}=K_d(AB)/[K_d(AA)^{1/2}\times K_d(BB)^{1/2}]$$

where $K_d$ (AB), $K_d$ (AA) and $K_d$ (BB) are the dissociation constants of the probe/target heterodimer, the probe homodimer and the target homodimer, respectively.

The dissociation constant for each dimer is determined so that the degree of specificity, $\Delta G_{spec}$, given by —RTln$K_{spec}$, could be estimated. A dissociation constant is determined, for example, by fitting the urea dependent circular dichroism (CD) signal as a function of urea concentration to a monomer-dimer equilibrium. An estimate of the dissociation constant for each homodimer is obtained from measurements of the helical CD signal as a function of peptide concentration.

Alternatively, specificity may also be determined by measuring $\Delta T_m$, i.e., the difference between the $T_m$ of the heterodimer and the average of the $T_m$ values for the homodimers as described by O'Shea et al., (1992) *Cell* 66:699–708. This $\Delta T_m$ difference has been measured for disulfide-bonded leucine-zipper peptides and has been shown to be related to $\Delta G_{spec}$ by a proportionality constant of 7.4° C./kcal $mol^{-1}$ (O'Shea et al. (1992) supra).

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); TLC (thin layer chromatography);

Example 1

Determination of the Amino Acid Pairing Preferences at Positions a and d of the Repeating Heptad in a Coiled Coil Region Using the Coiled Coils in Keratin Proteins In order to determine the pairing preference at positions a and d in the repeating heptad of a coiled coil region, pairing frequencies at these positions in obligate heterodimers were calculated. This approach was based on the assumption that the four heptad positions that make interhelical contacts in the coiled coil region are most likely to determine pairing specificity. While experiments can be envisioned to measure the free energies of heterotypic contacts, a simpler initial approach of calculating residue pair frequencies at positions a, d, e and g in the sequences of heterodimers was first adopted. These pair frequencies were expected to reveal the pairing preferences that form the basis for heterotypic associations.

The number of obligate heterodimer sequences is limited, and those in which the register of the helices is known is even more restricted. The human heterodimers K1–K10, K5–K14, K4–K13, and K6–K16 were selected because they form obligate heterodimers and because the amino acid sequence for each of these proteins is known. In addition, the four distinct coiled-coil domains in the epidermal keratins mediate formation of specific heterodimers, even when multiple keratin sequences are expressed in a particular cell. The sequence homologies between the four coiled-coil segments in each keratin chain allowed the register (i.e., the matrix of pairing frequencies) to be deduced unambiguously.

The amino acid sequences were analyzed by eye and the heptad positions assigned based on the characteristic 3,4 spacing of hydrophobic residues. Three residues separated successive a and d positions, and four residues separated each d position from the next a position (the heptad positions in the sequences of type I and type II obligate heterodimers of keratins were subsequently confirmed using the program PAIRCOIL (Berger et al. (1995)). To analyze these assignments for preferred heteromeric pairs at the a, d, e and g positions, a short awk script was written to calculate the probability that each observed pairing frequency arose by random association. Segments with different hydrophobic spacings, the so-called stutter motifs, were excluded from the analysis.

By tabulating the frequency of each amino acid contact in the a, d, e and g positions, 20×20 preference matrices were obtained (Tables 2–5).

TABLE 2

Frequency of a:a' and d:d' Interactions in Human Keratins

| | | a | | | | | | | | | | | | | | | | | | | | | |
|---|---|---|---|---|---|---|---|---|---|---|---|---|---|---|---|---|---|---|---|---|---|---|---|
| | | A | C | D | E | F | G | H | I | K | L | M | N | P | Q | R | S | T | V | W | Y | | |
| | | 0 | 0 | 1 | 0 | 0 | 0 | 1 | 3 | 0 | 0 | 0 | 0 | 0 | 0 | 0 | 0 | 0 | 4 | 0 | 0 | A | |
| | | | 0 | 0 | 0 | 0 | 0 | 0 | 0 | 3 | 0 | 0 | 0 | 0 | 0 | 0 | 0 | 0 | 0 | 0 | 0 | C | |
| | Y | 4 | | 0 | 0 | 0 | 0 | 0 | 0 | 0 | 0 | 0 | 0 | 0 | 0 | 0 | 0 | 0 | 0 | 0 | 0 | D | |
| | W | 0 | 0 | | 0 | 0 | 0 | 0 | 0 | 0 | 0 | 0 | 0 | 0 | 0 | 0 | 0 | 0 | 0 | 0 | 3 | E | |
| | V | 2 | 0 | 0 | | 0 | 0 | 1 | 2 | 0 | 4 | 1 | 0 | 0 | 0 | 0 | 0 | 0 | 1 | 0 | 0 | F | |
| | T | 0 | 0 | 1 | 0 | | 0 | 0 | 0 | 0 | 0 | 0 | 0 | 0 | 0 | 0 | 0 | 0 | 0 | 0 | 0 | G | |
| | S | 1 | 0 | 0 | 2 | 0 | | 0 | 0 | 0 | 0 | 0 | 0 | 0 | 0 | 0 | 0 | 0 | 0 | 0 | 2 | H | |
| | R | 0 | 0 | 0 | 0 | 0 | 0 | | 9 | 1 | 26 | 5 | 1 | 0 | 0 | 2 | 2 | 0 | 5 | 3 | 1 | I | |
| | Q | 0 | 0 | 3 | 0 | 0 | 0 | 0 | | 5 | 1 | 1 | 1 | 0 | 0 | 2 | 0 | 0 | 0 | 0 | 0 | K | |
| | P | 1 | 0 | 0 | 0 | 0 | 0 | 0 | 0 | | 14 | 4 | 0 | 0 | 0 | 0 | 2 | 1 | 5 | 0 | 0 | L | |
| | N | 0 | 0 | 0 | 0 | 0 | 0 | 0 | 0 | 0 | | 2 | 0 | 0 | 0 | 1 | 0 | 0 | 0 | 0 | 0 | M | |
| d | M | 0 | 0 | 3 | 0 | 0 | 0 | 1 | 0 | 0 | 0 | | 4 | 0 | 0 | 3 | 1 | 0 | 0 | 0 | 3 | N | a' |
| | L | 0 | 4 | 6 | 0 | 0 | 1 | 3 | 1 | 1 | 3 | 51 | | 0 | 0 | 0 | 0 | 0 | 0 | 0 | 0 | P | |
| | K | 0 | 0 | 0 | 0 | 0 | 0 | 0 | 0 | 0 | 0 | 0 | 0 | | 0 | 0 | 0 | 0 | 1 | 0 | 0 | Q | |
| | I | 0 | 0 | 0 | 0 | 1 | 0 | 1 | 0 | 0 | 3 | 3 | 0 | 0 | | 3 | 0 | 0 | 0 | 0 | 0 | R | |
| | H | 0 | 0 | 0 | 0 | 0 | 0 | 0 | 0 | 4 | 0 | 0 | 0 | 0 | 0 | | 0 | 0 | 1 | 0 | 1 | S | |
| | G | 0 | 0 | 0 | 1 | 0 | 0 | 0 | 0 | 0 | 1 | 0 | 0 | 0 | 0 | 0 | | 0 | 0 | 0 | 2 | T | |
| | F | 9 | 0 | 0 | 0 | 0 | 0 | 0 | 0 | 0 | 0 | 0 | 0 | 0 | 0 | 0 | 3 | | 7 | 0 | 0 | V | |
| | E | 0 | 0 | 0 | 0 | 0 | 1 | 2 | 0 | 0 | 0 | 0 | 0 | 0 | 0 | 0 | 1 | 9 | | 0 | 0 | W | |
| | D | 0 | 0 | 0 | 0 | 0 | 0 | 0 | 0 | 0 | 0 | 4 | 0 | 0 | 0 | 0 | 0 | 0 | 0 | | 10 | Y | |
| | C | 0 | 0 | 0 | 0 | 0 | 0 | 0 | 0 | 0 | 0 | 0 | 0 | 0 | 0 | 0 | 0 | 0 | 0 | 0 | | | |
| | A | 0 | 0 | 3 | 0 | 0 | 0 | 0 | 0 | 3 | 3 | 7 | 1 | 7 | 0 | 0 | 0 | 0 | 0 | 0 | 0 | | |
| | | Y | W | V | T | S | R | Q | P | N | M | L | K | I | H | G | F | E | D | C | A | | |
| | | | | | | | | | | | d' | | | | | | | | | | | | |

Table 2 shows a reference matrix for the amino acids at positions a and d. The letters A, C, D etc. represent the single letter abbreviation of each of the 20 amino acids which were found to be located at the a, a', d, and d' positions. The arabic numerals inside Table 2 represent the frequency at which a combination of two amino acids were found to be located at the a:a' positions (right hand triangle of Table 2) and at the d:d' positions (left hand triangle of Table 2). Frequencies on the diagonals denote homotypic amino acid pairs in the heterodimer sequences. Amino acids with a high relative frequency of heterotypic pairing and a low relative frequency of homotypic pairing—such as ala, ile, met and ser at the a position and ala, phe, his, ile, met, asn and val at the d position—provide evidence that core residues can confer specificity to coiled-coil dimerization.

Thus, Table 2 shows that certain amino acid residues never pair with like residues in the keratin core sites (e.g. alanine and histidine at the d position; alanine and serine at the a position). This observation suggested that a and d residues can influence heterospecificity. The preponderance of leucine:isoleucine and methionine:isoleucine pairs at the a positions also suggested that these combinations favored heterodimerization.

The g:e' interactions in type I keratin homodimers (Table 3), in type II keratin homodimers (Table 4), and in keratin heterodimers composed of one type 1 and one type 2 chains (Table 5) were compared as to the frequency of repulsive, attractive and hydrogen bonds.

TABLE 3

Frequency of g:e' Interactions in Type I Keratin Homodimers eg-pair:

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| 0 | 0 | 0 | 3 | 0 | 0 | 0 | 5 | 0 | 0 | 0 | 0 | 0 | 5 | 0 | 0 | 1 | 0 | 0 | 0 | A |
| | 0 | 0 | 0 | 0 | 0 | 0 | 0 | 0 | 0 | 0 | 0 | 0 | 0 | 0 | 0 | 0 | 0 | 0 | 0 | C |
| | | 0 | 2 | 0 | 0 | 0 | 0 | 4 | 5 | 0 | 1 | 0 | 4 | 2 | 0 | 0 | 0 | 0 | 5 | D |
| | | | 1 | 0 | 0 | 0 | 0 | 24 | 3 | 0 | 8 | 0 | 7 | 2 | 2 | 2 | 0 | 0 | 0 | E |
| | | | | 0 | 0 | 0 | 0 | 0 | 1 | 0 | 0 | 0 | 1 | 0 | 0 | 0 | 0 | 0 | 0 | F |
| | | | | | 0 | 0 | 0 | 1 | 5 | 2 | 0 | 0 | 2 | 0 | 1 | 3 | 0 | 0 | 0 | G |
| | | | | | | 0 | 0 | 0 | 0 | 0 | 0 | 0 | 0 | 0 | 0 | 0 | 0 | 0 | 0 | H |
| | | | | | | | 0 | 12 | 1 | 0 | 1 | 0 | 1 | 2 | 0 | 0 | 0 | 0 | 0 | I |
| | | | | | | | | 0 | 4 | 2 | 2 | 0 | 5 | 1 | 2 | 1 | 0 | 0 | 0 | K |
| | | | | | | | | | 2 | 0 | 0 | 0 | 2 | 4 | 0 | 5 | 0 | 0 | 0 | L |
| | | | | | | | | | | 0 | 0 | 0 | 0 | 4 | 0 | 0 | 0 | 0 | 0 | M |
| | | | | | | | | | | | 0 | 0 | 8 | 0 | 0 | 0 | 0 | 0 | 0 | N |
| | | | | | | | | | | | | 0 | 0 | 0 | 0 | 0 | 0 | 0 | 0 | P |
| | | | | | | | | | | | | | 5 | 1 | 0 | 0 | 2 | 0 | 0 | Q |
| | | | | | | | | | | | | | | 0 | 0 | 1 | 1 | 0 | 9 | R |
| | | | | | | | | | | | | | | | 0 | 0 | 0 | 0 | 0 | S |
| | | | | | | | | | | | | | | | | 0 | 0 | 0 | 0 | T |
| | | | | | | | | | | | | | | | | | 0 | 0 | 0 | V |
| | | | | | | | | | | | | | | | | | | 0 | 0 | W |
| | | | | | | | | | | | | | | | | | | | 0 | Y |

Repulsives: 4 Attractives: 32 H-bonds(?): 98

TABLE 4

Frequency of g:e' Interactions in Type II Keratin Homodimers eg-pair:

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| 0 | 0 | 0 | 5 | 0 | 0 | 0 | 0 | 1 | 2 | 0 | 0 | 0 | 5 | 5 | 0 | 0 | 1 | 0 | 0 | A |
| | 0 | 0 | 0 | 0 | 0 | 0 | 0 | 0 | 0 | 0 | 0 | 0 | 0 | 0 | 0 | 0 | 0 | 0 | 2 | C |
| | | 0 | 0 | 0 | 0 | 0 | 0 | 0 | 2 | 0 | 0 | 0 | 0 | 5 | 0 | 0 | 1 | 0 | 0 | D |
| | | | 1 | 0 | 0 | 0 | 3 | 8 | 9 | 5 | 1 | 0 | 0 | 7 | 5 | 6 | 1 | 0 | 0 | E |
| | | | | 0 | 0 | 0 | 0 | 0 | 0 | 0 | 0 | 0 | 0 | 0 | 0 | 0 | 0 | 0 | 0 | F |
| | | | | | 0 | 0 | 0 | 0 | 2 | 1 | 0 | 0 | 1 | 1 | 0 | 0 | 0 | 0 | 0 | G |
| | | | | | | 0 | 0 | 0 | 1 | 0 | 0 | 0 | 0 | 0 | 0 | 0 | 0 | 0 | 0 | H |
| | | | | | | | 0 | 3 | 0 | 0 | 0 | 0 | 4 | 8 | 0 | 1 | 1 | 0 | 0 | I |
| | | | | | | | | 0 | 4 | 2 | 4 | 0 | 4 | 0 | 2 | 6 | 1 | 0 | 1 | K |
| | | | | | | | | | 0 | 0 | 1 | 1 | 1 | 11 | 3 | 5 | 0 | 0 | 0 | L |
| | | | | | | | | | | 0 | 4 | 0 | 2 | 0 | 0 | 0 | 0 | 0 | 1 | M |
| | | | | | | | | | | | 0 | 0 | 1 | 0 | 0 | 5 | 2 | 0 | 0 | N |
| | | | | | | | | | | | | 0 | 0 | 0 | 0 | 0 | 0 | 0 | 0 | P |
| | | | | | | | | | | | | | 0 | 4 | 0 | 4 | 0 | 0 | 2 | Q |
| | | | | | | | | | | | | | | 0 | 0 | 3 | 1 | 0 | 1 | R |
| | | | | | | | | | | | | | | | 0 | 0 | 0 | 0 | 0 | S |
| | | | | | | | | | | | | | | | | 0 | 5 | 0 | 0 | T |
| | | | | | | | | | | | | | | | | | 0 | 0 | 0 | V |
| | | | | | | | | | | | | | | | | | | 0 | 0 | W |
| | | | | | | | | | | | | | | | | | | | 0 | Y |

Repulsives: 1 Attractives: 20 H-bonds(?): 81

TABLE 5

Frequency of g:e' Interactions in Keratin Heterodimers eg-pair:

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| 1 | 0 | 3 | 2 | 0 | 0 | 0 | 5 | 7 | 2 | 0 | 1 | 0 | 11 | 0 | 0 | 0 | 0 | 0 | 0 | A |
| | 0 | 0 | 0 | 0 | 0 | 0 | 0 | 0 | 0 | 0 | 0 | 0 | 0 | 0 | 0 | 0 | 0 | 0 | 2 | C |

TABLE 5-continued

Frequency of g:e' Interactions in Keratin Heterodimers eg-pair:

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| | | 1 | 2 | 0 | 0 | 0 | 5 | 6 | 3 | 0 | 1 | 0 | 0 | 4 | 0 | 6 | 0 | 0 | 0 | D |
| | | | 1 | 0 | 4 | 0 | 2 | 29 | 13 | 4 | 8 | 0 | 11 | 17 | 6 | 4 | 2 | 0 | 1 | E |
| | | | | 0 | 0 | 0 | 0 | 0 | 0 | 1 | 0 | 0 | 0 | 0 | 0 | 0 | 0 | 0 | 1 | F |
| | | | | | 0 | 0 | 0 | 1 | 5 | 3 | 0 | 0 | 1 | 2 | 0 | 0 | 2 | 0 | 0 | G |
| | | | | | | 0 | 0 | 0 | 1 | 0 | 0 | 0 | 0 | 0 | 0 | 0 | 0 | 0 | 0 | H |
| | | | | | | | 0 | 10 | 0 | 0 | 2 | 0 | 1 | 15 | 0 | 1 | 0 | 0 | 1 | I |
| | | | | | | | | 2 | 12 | 4 | 5 | 0 | 7 | 1 | 1 | 4 | 3 | 0 | 0 | K |
| | | | | | | | | | 0 | 2 | 5 | 1 | 8 | 10 | 3 | 10 | 1 | 0 | 0 | L |
| | | | | | | | | | | 0 | 0 | 0 | 7 | 1 | 0 | 1 | 0 | 0 | 0 | M |
| | | | | | | | | | | | 0 | 0 | 9 | 1 | 0 | 6 | 0 | 0 | 0 | N |
| | | | | | | | | | | | | 0 | 0 | 0 | 0 | 0 | 0 | 0 | 0 | P |
| | | | | | | | | | | | | | 4 | 2 | 1 | 7 | 1 | 0 | 2 | Q |
| | | | | | | | | | | | | | | 0 | 1 | 6 | 3 | 0 | 10 | R |
| | | | | | | | | | | | | | | | 0 | 3 | 0 | 0 | 0 | S |
| | | | | | | | | | | | | | | | | 0 | 0 | 0 | 0 | T |
| | | | | | | | | | | | | | | | | | 0 | 0 | 4 | V |
| | | | | | | | | | | | | | | | | | | 0 | 0 | W |
| | | | | | | | | | | | | | | | | | | | 0 | Y |

Repulsives: 7  Attractives: 56  H-bonds(?): 186

Paradoxically, oppositely charged residues occurred at g and succeeding e' positions with approximately equal frequencies in each keratin heterodimer and the homodimers of its constituent chains. Table 5 showed the presence of 56 attractive pairs in the heterodimers. This number was similar to the total number (i.e., 20 and 32) of repulsive pairs observed in the constituent homodimers (Tables 3 and 4). The individual pairs of chains showed the same trend. The number of repulsive g-e pairs was also similar in the homodimers and heterodimers. This pattern was at odds with experiments showing that complementary charges at g and succeeding e' positions in heterodimers, coupled with repulsive g-e' charge pairs in the constituent homodimers, could favor heterotypic pairing. Consequently, the results demonstrated that the keratins achieve heterospecificity primarily by core pairing and by changes in the context of g-e' ion pairs.

The pairing preference data for a:a' amino acids and d:d' amino acids shown in Table 2, in combination with the known principle of repulsive interactions relieved by charge complementation at g and succeeding e' positions was used to design and synthesize a polypeptide probe capable of heterospecific binding to a target polypeptide sequence.

Example 2

Design and Synthesis of a Polypeptide Probes (anti-APCp1 and anti-APCp2) Specific for APC The coiled coil domain of the APC tumor suppressor protein was chosen as a target for the peptide probe design. Mutations in the APC gene are associated with 75% of inherited and sporadic colon tumors (Nakamura, *J. Cancer Res. Clinical Onco.* 121, 529–34 (1995)). Additionally, APC is known to bind and down regulates β-catenin, suggesting a role in regulation of cell adhesion. (Munemitsu et al., *Proc. Natl. Acad. Sci. USA* 92, 3046–3050 (1995); Rubinfeld et al., *Science* 262, 1741–43 (1993); Polakis, *Curr. Op. Genetics and Development* 5, 66–71 (1995)). Disease-associated APC alleles usually encode truncated, prematurely terminated proteins. (Joslyn et al., *Proc. Natl. Acad. Sci. USA* 90, 11109–11113 (1993); Groden et al., *Cancer Res.* 55, 1531–9 (1995); Polakis (1995)), therefore the tumorigenic proteins contain the coiled-coil domain targeted by our anti-APC peptide. Groden (1991); Joslyn (1993).

Most importantly, the amino-terminal 55 amino acids of the APC protein contain a coiled coil motif and mediate homodimerization of APC fragments as a parallel coiled coil. Joslyn (1993). Since this 55 amino acid region is present in all the truncated forms of the APC protein, both the wild-type form and all the truncated transforming alleles of APC contain the coiled coil domain that is the target of the probe.

A. Principles of Designing a Polypeptide Probe Specific for the Coiled Coil Region of APC The design of the polypeptide probe specific for APC was based on the amino acid sequence (SEQ ID NO: 1) (GenBank Accession No. M73548) of amino acids 2–55 of wild type APC (APC-55). The APC-55 sequence was specified by expression of a nucleic acid fragment encoding this sequence, and the molecular mass of the polypeptide expression product was verified as follows. APC-55, a peptide corresponding to amino acids 2–55 of human APC, was produced by expression in *E. coli* (Joslyn et al., 1993). The gene fragment encoding this sequence was inserted between the NdeI and BamH1 sites in the pAED4 plasmid, and BL21 (DE3) cells were transformed by the $CaCl_2$ method. Fresh transformants were grown in LB medium to $OD_{600}$=0.8 and induced with 1 mM IPTG. Cells were harvested after five hours and stored at −70° C. Thawed cell pellets were resuspended in 80 mM TrisHCl pH8.0, 0.2 mM EDTA, 20 mM KCl and lysed by sonication in a dry ice/ethanol bath. The pH was lowered to 2 by dropwise addition of concentrated HCl, and the acidified lysate was cleared by centrifugation.

The supernatant was neutralized, diluted two-fold and loaded onto DEAE cellulose. The column was developed with 10–1000 mM KCl. The peak fractions of peptide were concentrated and purified by reverse phase HPLC on a C18 semiprep column (Vydac). A 0.2%/min gradient of 0.1% TFA eluted a single peak. The peak fractions were lyophilized and resuspended in water. The amino acid composition of the peptide was confirmed by electrospray mass spectrometry. The sequence of APC-55 was determined to be MAAASYDQLLKQVEALKMENSNLRQELED NSNHLTKLETEASNMKEVLKQL QGSI (SEQ ID NO: 1). The underlined residues correspond to amino acids that were targeted for change in the design of the anti-APC peptide.

As explained in the Detailed Description above, two general principles were used to introduce specificity into the APC peptide probe. The first guiding principle was that core residues were chosen to conserve packing volume and to introduce a:a' and d:d' pairs that occur at enhanced frequency in the sequences of keratin heterodimers as shown in Table 2. The second guiding principle was that charged residues were placed at e and g positions in the probe to form favorable electrostatic interactions with apposed g' and e' residues in the target and, at the same time, to form repulsive interactions with apposed g' and e' residues in the probe. Thus, destabilizing interactions were introduced into the probe that could be relieved in the heterodimer.

In addition to these two guiding principles, additional changes at the f positions were made to change the overall charge of the probe to facilitate experimental analysis of pairing, to preserve the overall stability of the system using residues with significant helical propensity, to promote the solubility of the probe peptide, and to introduce chromogenic groups to allow the probe to be detected optically. These changes were not expected to contribute to the preference of the anti-APC peptide for its target. Based on the above, altogether 20 changes from the wild type APC sequence were made to generate anti-APCp1 and anti-APCp2 peptides.

TABLE 6

Design Rationale for Sequence-Specific anti-APC

| Residue | Change | Rationale |
|---|---|---|
| Met1 | | Absent in purified APC-55 due to cleavage in vivo |
| Ala2 | Met/Nrl | Complement core packing defect* |
| Ser5 | Lys | Destabilize anti-APC homodimer (+/+ with Lys10) |
| Tyr6 | Gly | Complement core packing defect* |
| Leu10 | Lys | Destabilize anti-APC homodimer (+/+ with Lys5) |
| Gln12 | Glu | Stabilize Heterodimer (+/− Lys17) Destabilize anti-APC homodimer (−/− with Glu17) |
| Lys17 | Glu | Destabilize anti-APC homodimer (−/− with Glu12) |
| Met18 | Tyr | Chromophore |
| Gln25 | Lys | Increase helical propensity and net charge |
| Glu26 | Lys | Destabilize anti-APC homodimer (+/+ with Lys31) |
| Asn30 | His | Complement core packing defect* |
| Ser31 | Lys | Stabilize heterodimer (+/− with Glu26) Destabilize anti-APC homodimer (+/+ with Lys26) |
| Asn32 | Lys | Increase helical propensity and net charge |
| His33 | Lys | Stabilize heterodimer (+/− with Glu38) Destabilize anti-APC homodimer (+/+ with Lys38) |
| Glu38 | Lys | Destabilize anti-APC homodimer (+/+ with Lys33) |
| Ala41 | Ile | Complement core packing defect* |
| Met44 | Ala | Complement core packing defect* |
| Glu46 | Lys | Increase helical propensity and net charge |
| Val47 | Met/Nrl | Heterospecificity (interacts with Gln52)* |
| Gln52 | Tyr | Heterospecificity (interacts with Val47)* |
| Gly53 | Ala | Increase helical propensity |

*Changes based on analysis of keratin coiled-coil sequences.

Statistically preferred pairs were compared to the wild-type APC-55 sequence, and five changes were made to the a and d positions in the probe, Ala2Met/Nrl, Tyr6Gly, Asn30His, Ala41Ile and Met44Ala (Table 6). Four pairs of sequence changes were made to destabilize probe/probe oligomerization with repulsive charge/charge interactions Ser5Lys, Leu10Lys, Gln12Glu, Lys17Glu, Glu26Lys, Ser31Lys, His33Lys, and Glu38Lys. These unfavorable repulsive interactions were designed to be alleviated by heterodimerization with the APC peptide. Two additional changes at the e and g positions were made in order to increase heterospecificity: Val47Met/Nrl and Gln52Tyr. Woolfson (1995).

Asn20, at an a position, remained in both peptides to facilitate an interhelical buried polar interaction often observed in coiled coils (Alber (1992)) and has been proposed to aid specificity in chain orientation and heptad alignment. Lumb, 1995. Gln25, Asn32, and Glu46 (all found in the f position) were changed to Lys in the probe in order to increase helical propensity (O'Neil et al., *Science* 250, 646–651 (1990)) and the net charge of the probe for solubility. Gly53 (an f position) was also changed to Ala in order to increase helical propensity. Finally, Met18 (also an f position) was changed to a Tyr in order to add a chromophore to aid in concentration determination. As discussed above, the changes at the b, c and f positions were not expected to influence the specificity (i.e., pair preference) of the probe.

Based on the above rationale, the anti-APCp1 probe sequence was MAAKGDQLKKEVEALEYENSNLR KKLEDHKKKLTKLKTEISNAKKMLKQLYASI (SEQ ID NO: 2). Changes from the wild type sequence are underlined. The first-designed anti-APC sequence (anti-APCp1) contained methionine residues at two positions. This peptide was specific for the N-terminal APC coiled coil, as judged by thermal denaturation experiments showing thermal stability at 20 μM peptide as a function of concentration in the presence of equimolar amounts of APC (Table 7).

TABLE 7

Concentration Dependence on Thermal Stability

| Peptide | Apparent $T_m$* (° C.) 8.0 μM | 20.0 μM | 75.0 μM |
|---|---|---|---|
| APC-55 | 36.3 | 40.0 | 46.5 |
| Anti-APCp1 | 45.0 | 52.3 | 59.6 |
| APC-55/Anti-APCp1 | 50.6 | 54.3 | 64.7 |

*calculated from the midpoint of transition of thermal denaturation curves generated by CD spectroscopy at 222 nm. Samples are in 10 mM phosphate pH 7.0 and 100 mM potassium flouride.

However, the methionine side chain was found to be subject to oxidation. To block oxidation the methionines were replaced with the nonbiological, isoteric amino acid, norleucine to generate anti-APCp2 [NrlAAKGDQLKKEVEALEYENSNLRKKLEDHKKK LTKLKTEISNAKKNrlLKQ LYASI (SEQ ID NO: 3); the underlined amino acid is norleucine].

Anti-APCp1 and anti-APCp2 were identical except that Met2 and Met47 in anti-APCp1 were replaced by the nonbiological, isosteric Nrl residue in anti-APCp2. These changes were made to eliminate the possibility of oxidation of the methionines at positions 2 and 47. The anti-APCp1 is capable of being produced in vivo, while anti-APCp2 can be produced only by chemical synthesis.

FIG. 2 provides a Helical wheel diagram showing the sequences of the target APC-55 peptide (left) and the designed anti-APCp2 probe (right). The residues in the wild-type APC-55 peptide are shown in outlined letters, and the sequence changes in anti-APCp2 are shown in bold. The sequences begin with Ala2 (APC-55) and Nrl2 (anti-APCp2) are position d. The view is from amino-terminus along the superhelical axis. The a and d residues form alternating layers, and potential interhelical ion pairs between g and succeeding e' residues are marked with arrows. As explained above, of the 20 changes in anti-APCp2, five were made based on covariation frequencies (Table 2) and eight changes at the e and g positions were made to introduce repulsive ionic interactions in the anti-APC homodimer that are relieved in the parallel heterodimer. Two additional changes at the e and g positions and five changes at the non-interacting f position were made to add chromophores or to increase the helical propensity or the net charge of the designed peptide.

The anti-APCp2 was also demonstrated to be specific for the N-terminal APC coiled coil, as judged by the absence of concentration dependent thermal stability of the hetero-oligomer of anti-APC-p2 and APC-55 (Table 8).

TABLE 8

Thermal stability at 20 μM peptide concentration in PBS (pH 7.0)

| Peptide | APC-55 | anti-APCp1 | anti-APCp2 | APC + anti-APCp | APC + anti-APCp2 |
|---|---|---|---|---|---|
| Tm(° C.) | 40.0 | 52.3 | 58.2 | 54.3 | 57.5 |

As noted above, FIG. 2 shows the amino acids at each of the a, b, c, d, e, f, and g positions of APC-55 (open letters) and the amino acids at each of the a', b', C', d', e', f, and g' positions of the designed anti-APCp2. The replacement of methionine with norleucine caused the denaturation temperature of the anti-APC peptide to rise, but the anti-APCp2 peptide still showed specificity for APC (Table 8). These results demonstrate that the nonbiological amino acid, norleucine, was not necessary to achieve the preference of the probe for APC.

B. Peptide Synthesis and Purification

Following the design of the anti-APCp1, the anti-APCp1 and anti-APCp2 polypeptides as well as the APC-55 polypeptide were synthesized with F-moc chemistry using an Applied Biosystems 581A peptide synthesizer. As noted above, methionines in anti-APCp1 were replaced with isosteric norleucine (Nrl) in anti-APCp2 to prevent oxidation of the side chain. Peptides were cleaved from the resin with hydrofluoric acid (HF), lyophilized, resuspended in water and purified by reverse phase HPLC using the same column and gradient as for the wild-type sequence. The amino acid composition and purity of the peptides were checked by HPLC analysis and electrospray mass spectrometry.

Example 3

The anti-APCp1 and Anti-APCp2 Polypeptide Probes Bind Specifically to APC and Preferentially Form Hetero-oligomers To determine whether the anti-APCp1 and anti-APCp2 polypeptide probes bind specifically to APC and whether they form hetero-oligomers with APC in preference to homo-oligomers, the interactions between the probes and APC were examined using (a) circular dichroism spectroscopy, (b) equilibrium ultracentrifugation, and (c) native gel electrophoresis as follows.

A. Circular Dichroism Spectroscopy

Figure 4:
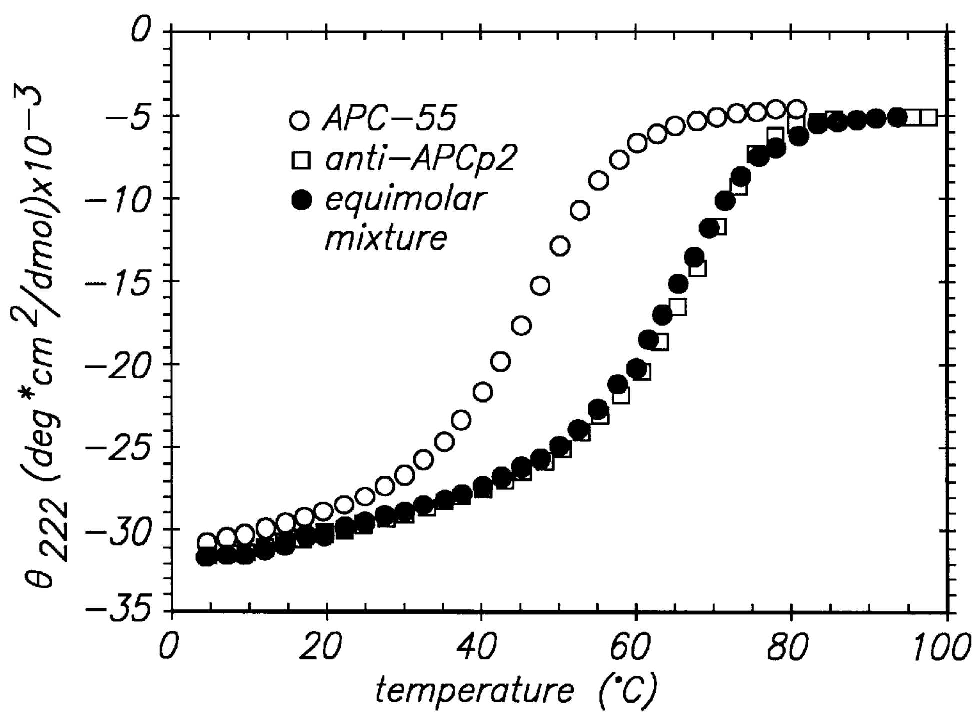
FIG. 4 shows the thermal denaturation of APC-55, anti-APCp2, and an equimolar mixture of APC-55 and anti-APCp2.

CD spectra (180–300 nm) for the APC-55 and anti-APCp1 peptides alone and in combination were recorded in a 1 mm quartz cuvette at 5° C. using an Aviv 62DS circular dichroism spectrophotometer. The concentrations of peptide stocks were determined optically by the method of Gill and vonHippel, *Anal. Biochem* 182:319–326 (1989). Peptide stocks were diluted in 10 mM $KPO_4$, 100 mM KF, pH 7.0. Thermal denaturations were carried out in steps of 1–3° C. with 2 minutes for equilibration and one minute for data averaging. Thermal transitions were >95% reversible. The data are shown in FIGS. 3 and 4. The results in FIGS. 3 and 4 obtained with the APC-55 alone are shown by open circles (○), with the anti-APCp1 alone by squares (□), and with an equimolar mixture of APC-55 and anti-APCp1 with closed circles (●).

The results demonstrate that the designed peptide probe, and an equimolar mixture of the probe and the wild-type APC-55 peptide were at least 95% helical at 75 μM. Thermal denaturation experiments followed by circular dichroism at 222 nm demonstrated an increase greater than 10° C. in the thermal melting transition when the APC-55 peptide and the probe were mixed in equal amounts.

The stability of the hetero-oligomerization was determined by the investigation of the dependence of apparent $T_m$ on peptide concentration. These results are shown in Table 9.

TABLE 9

Dependence of apparent Tm on peptide concentration.

| | Apparent Tm (+/− 1.25° C.) | | |
|---|---|---|---|
| Peptide | 8.0 μM | 20.0 μM | 75.0 μM |
| APC-55 | 36.3 | 40.0 | 46.5 |
| anti-APCp2 | 51.5 | 58.6 | 66.4 |
| APC-55/anti-APCp2 | 52.9 | 57.5 | 63.6 |

The higher thermal stability of the heteromeric mixture was consistently observed at different peptide concentrations (Table 9). The observed increase in $T_m$ with increasing peptide concentration is consistent with the formation of oligomers.

B. Equilibrium Ultracentrifugation

The APC-55 and anti-APCp1 peptides alone and in combination were analyzed by equilibrium centrifugation using a Beckman X-LA ultracentrifuge. Samples were analyzed at three total peptide concentrations (0.075, 0.150, and 0.250 mM) in 10 mM $KPO_4$, 100 mM KF, pH 7.0. Absorbance was monitored at 215, 230 and 280 nm. Solvent density was assumed to be 1.0005 g/l at 278° K. Partial specific volumes were calculated from the amino acid compositions of the peptides. Apparent molecular weights were calculated by simultaneously fitting all data sets for one species to a single molecular weight with the program HID4000. The results of the equilibrium ultracentrifugation are shown in Table 10.

TABLE 10

Molecular weights determined by ultracentrifugation

| Peptide | calculated MW | observed MW |
|---|---|---|
| APC-55 | 12,200 | 12,400 |
| anti-APCp2 | 12,500 | 14,000* |
| APC-55/anti-APCp2 | 12,300 | 13,300 |

*Systematic residuals indicate multiple oligomeric species

The results shown in Table 10 confirmed the heteromeric mixture to be a dimer, consistent with the dimeric coiled coil design (Table 6). Importantly, the probe by itself did not form a single oligomeric species in solution as shown by the observed molecular weight of 14,000 (Table 10). This demonstrated that the anti-APCp2 polypeptide forms homo-oligomers other than and in addition to a homodimer. The additional observation that the anti-APCp2 polypeptide, which forms homodimers as well as homotrimers, and possibly homotetramers, was capable of hetero-dimerization with APC-55 demonstrates that a coiled coil polypeptide probe containing more than two polypeptide strands is capable of heterospecific oligomerization with a target coiled coil polypeptide.

C. Native Gel Electrophoresis

Native acrylamide gel electrophoresis was used as a direct test of heterodimer specificity. Samples of the individual peptides and an equimolar mixture of the peptides were prepared at 0.6 mM and diluted two-fold in 0.2% (w/v) methyl green, 20% glycerol, 750 mM beta-alanine acetate pH 6.0. Gels contained a separating gel of 7.5% acrylamide in 375 mM beta-alanine acetate, pH 4.0. Samples were run for 2.5 hours at 100 volts, and the gels were fixed with 2% glutaraldehyde and stained for at least 1 hour in 0.2% Coomassie Brilliant Blue in 50% methanol, 10% acetic acid (v/v). Destaining was carried out overnight in the same solvent lacking the dye.

Figure 5:
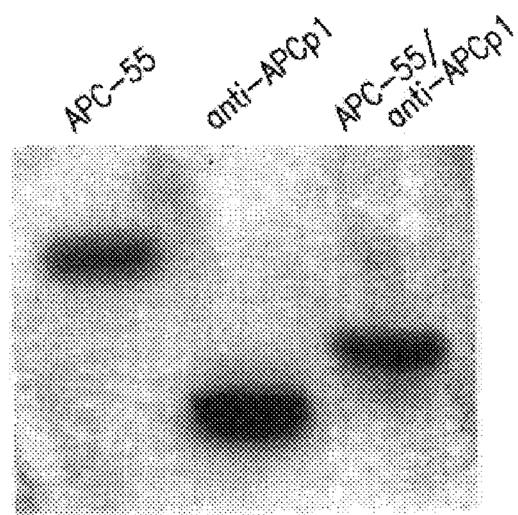
FIG. 5 shows native gel electrophoresis of APC-55, anti-APCp1 and a mixture of APC-55 and anti-APCp1.

The results of the native gel electrophoresis are shown in FIG. 5. FIG. 5C shows that when the heterodimer (an equimolar mixture of the two peptides) was used, a new single species with an intermediate mobility was detected. The new species had a mobility consistent with the calculated isoelectric point of the heterodimer (pI=10.0) The appearance of the heterodimeric species with concomitant loss of the homo-oligomers demonstrates the high specificity of the probe for the wild-type APC-55 peptide. This data also demonstrate that the preference for the formation of a heterodimer was at least 100 fold greater than the preference for the formation of homodimers as judged by the sensitivity of the detection method on native gels. The data presented herein was surprising in view of the prior art reports of the sufficiency of e':g interactions for dimerization specificity of coiled coil proteins [O'Shea et al. (1992), supra; O'Shea et al. (1993) supra; Krylov et al (1994) EMBO J. 13:2849–2861].

Further experiments to quantitate the level of specificity for heterodimerization of the anti-APCp2 probe with APC using fluorescence energy transfer titration by measuring the change in fluorescence between APC and buffer titrated with anti-APCp2 did not yield a numerical value for the heterodimerization specificity as the detection threshold of this method was greater than that necessary for such determination. Based on the sensitivity of the fluorescence method used, the dissociation constant of the APC-55/Anti-APCp2 heterodimer was estimated to be less than 10 nM. This high affinity demonstrates that the anti-APCp2 probe is useful at pharmacological concentrations.

Example 4

The anti-APC Polypeptide Probe is Heterospecific for APC in Bacterial Cell Lysates In order to test for dimerization specificity of the anti-APCp1 for APC fragments in the presence of many other cellular proteins, APC protein fragments were expressed in *E. coli* as fusion proteins with glutathione (GST). The specificity of binding of anti-APCp2 to APC was compared to the specificity of binding of a monoclonal anti-APC antibody on Western blots as follows. Cell extracts containing the fusion proteins were separated by SDS-PAGE and blotted. Biotinylated anti-APCp2 was used to detect these fusion proteins by binding the probe to the blotted APC fusion proteins and then developing the blot with streptavidin-HRP. Phosphorescence was detected on X-ray film. These steps are described more fully in the following sections.

A. Expression of APC Fusion Proteins

In frame, C-terminal fusions between APC sequences and glutathione S-transferase (GST) were constructed in the expression vector pGEX-2TK (Pharmacia). Enzymes for cloning were obtained from Life Technologies. The relevant sequence of each plasmid was confirmed using an Applied Biosystems 373A automated DNA sequencer.

i. pGEX-2TK/APC-H1

DNA encoding the first 55 amino acids of the human APC protein (heptad repeat 1) was PCR-amplified from a full length APC cDNA using Taq DNA polymerase and tailed primers that generated an EcoR1 cassette. (PCR primers: Forward-5'-TGTAAAACGACGGCCAGTGGAAT-TCATATGGCTGCAGCTT CAGTTG-3' (SEQ ID NO: 4); Reverse: 5'-CAGGAAACAGCTATGACCGAATTCCTAAATACTTCCTTGTAGTTGTTTA-3' (SEQ ID NO: 5)). The product and the vector were digested with EcoR1 and ligated.

ii. pGEX-2TK/APC-H1-4

An NdeI-SmaI DNA cassette encoding the N-terminal 373 amino acids of the APC protein (heptad repeats 1–4) was generated by restriction digestion of an APC cDNA construct in pBluescript. Following purification of the fragment by agarose gel electrophoresis, the NdeI overhang was filled in with Klenow DNA polymerase, and the resulting blunt-ended cassette was ligated into pGEX-2TK linearized with SmaI.

iii. pGEX-2TK/APC-PROBE

A BamH1-EcoR1 cassette encoding the anti-APCp1 probe peptide was created by synthesizing oligonucleotides to the 5' (probe5) and 3' (probe3) halves of anti-APCp1 gene sequence. The probe5 oligonucleotide was PCR-amplified using tailed primers to generate a double-stranded, BamH1-AvaII cassette, and the probe3 oligonucleotide was PCR-amplified with tailed primers to produce an AvaII-EcoR1 cassette. The probe 5 and probe3 cassettes were digested with AvaII, ligated and purified on a 6% polyacrylamide gel. The resulting anti-APCp1 gene and the vector were digested with BamH1 and EcoR1 and ligated.

iv. Bacterial cell lysates

Whole cell lysates were obtained by the method of Smith and Johnson (1988) from *E. coli* BL21 (DE3) expressing each of the GST fusion proteins. Bacteria carrying each pGEX-2TK-derived plasmid were cultured overnight at 37° C. in L broth supplemented with 50 mg/l ampicillin (Boerhinger Manheim). Overnight cultures were diluted 1:10 in fresh medium and grown an additional hour at 37° C. Expression of GST fusion proteins was induced by adding IPTG (ICN Biochemical) to a concentration of 0.1 mM. Induced cells were grown 3 hours at 37° C., harvested by centrifugation at 4° C., and washed in 10 ml PBS buffer (20 mM $NaPO_4$, 150 mM NaCl, pH 7.3). Cells were lysed by sonicating for 3×30 seconds in PBS containing 0.1% Triton X-100 (United States Biochemical), and the lysates were clarified by centrifugation. The supernatants containing GST alone and the GST-APC-H1 polypeptides were adjusted to a total protein concentration of 1 mg/ml in SDS PAGE sample buffer (62.5 mM TrisHCl, pH 6.8, 10% glycerol, 2% SDS, 0.7 mM 2-mercaptoethanol, 0.00125% bromophenol blue) and used for Western blotting analysis. The GST-APC-H1-4 and GST-APC-probe polypeptides were insoluble. The pellets from the lysates containing them were resuspended in PBS and adjusted to 1 mg/ml protein concentration in SDS PAGE sample buffer.

B. Western Blot Analysis

Bacterial lysates containing GST, GST-APC-H1, GST-APC-H1-4 and GST-APC-probe were diluted 1:10 in cell lysates from induced BL21 cells containing no APC sequences and adjusted to a final protein concentration of 0.5 mg/ml in sample buffer. Five micrograms of each sample was electrophoresed on a precast 10% Tricine-SDS polyacrylamide gel (Novex) as described by Schager and von-Jagow (1987). Proteins were transferred to 0.45 micron nitrocellulose for 2 hours at 100 V, 4° C., in transfer buffer (25 mM Tris, 192 mM glycine, 20% methanol, 0.1% SDS).

i. Detection using anti-APCp1 Sequences

The anti-APCp1 peptide was biotinylated by removing the F-moc protecting group from the N-terminus of the peptide on the synthesis resin and incubating the resin with the N-hydroxy-succinimidyl ester of biotin containing a long spacer arm (Pierce, Catalog #21336) in dimethylformamide. The biotinylated anti-APCp1 contains Met (instead of Nrl) as well as an additional Leu8Val mutation and Glu-Asp-Glu (wild-type APC sequence) at the peptide C-terminus. This probe was indistinguishable from anti-APCp1 in native gel experiments and CD experiments (data not shown). Blots were blocked for 1 hour in PNT buffer (10 mM phosphate, pH 8.0, 175 mM NaCl, 0.1% Tween-20) containing 0.5% bovine serum albumin. After blocking, blots were probed for I hour at 42° C. with 5 nM biotinylated antiAPC peptide in PNT buffer containing 1% BSA. After incubation for 30 minutes at room temperature in streptavidin-horseradish-peroxidase diluted 1:2000 in PNT plus 1% BSA, the blots were washed 3 times for 15 minutes in PNT buffer and developed using ECL substrate (Amersham).

ii. APC detection using APC Ab-1

Blots were blocked for 1 hour in TBST (10 mM phosphate, 175 mM NaCl, pH 8.0, 0.1% Tween-20) containing 5% BSA. After blocking, blots were probed with mouse monoclonal APC antibody Ab-1 (Oncogene Science/Calbiochem), which recognizes the N-terminal 55 amino acids of the APC protein (Smith K J, et al., (1993) *Proc. Natl. Acad. Sci USA* 90, 2846–2850). The antibody was diluted 1:3000 in TBST, 1% BSA. Blots were washed 3 times for 5 minutes each in TBST and incubated for 1 hour in horseradish peroxidase-conjugated rabbit anti-mouse $IgG_1$ antibody diluted 1:30000 in TBST, 1% BSA. After three 15-minute washes in TBST, blots were developed using ECL substrate (Amersham).

Figure 6A:
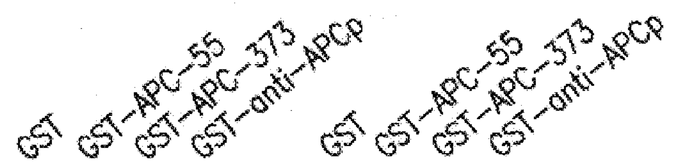
FIGS. 6A–C show blots of gels of expressed APC fusion proteins probed with anti-APC monoclonal antibody (A), anti-APCp1 polypeptide (B), and the Comassie Brilliant Blue stained gels used to prepare the blots (C).
Figure 6B:
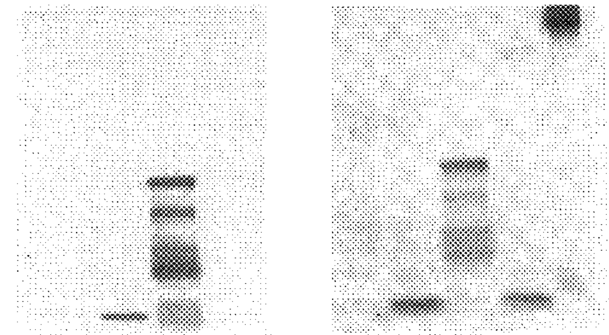
Figure 6C:
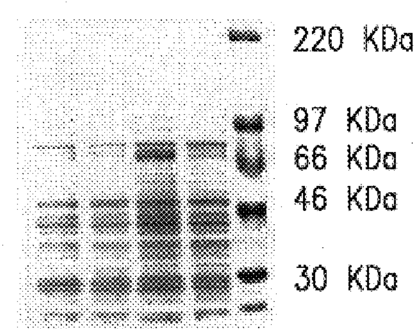

The results of the Western blot analysis are shown in FIG. 6. The SDS-PAGE prepared as described above is shown in FIG. 6C. This SDS-PAGE was blotted and the blots were developed with either biotinylated anti-APC monoclonal antibody (FIG. 6A) or biotinylated anti-APCp1 polypeptide probe (FIG. 6B). The results in FIG. 6 demonstrate that anti-APCp1 peptide can detect APC fragments with specificity even when all other *E. coli* proteins were present in the probed cell extract, thus demonstrating the specificity of the anti-APCp1 probe for APC.

Further, anti-APCp 1 and antibodies against the amino-terminus of APC detected similar patterns of GST-APC fusion proteins expressed in *E. coli* (FIG. 6). In particular, Western blots developed with the antisense peptide and the antibody revealed common regions of proteolytic susceptibility within the first 373 amino acids of APC. In contrast to the antibody, the anti-APCp1 peptide also bound to a GST fusion with the antisense sequence itself (FIG. 6B, lane 4). Thus, the twenty sequence changes in anti-APCp1 apparently abolished the antibody epitope but preserved the capacity for homo-oligomerization. These results suggest not only that the antisense peptide forms a coiled-coil interaction with the APC amino terminus, but also that this coiled coil forms in preference to interactions with *E. coli* proteins.

Example 5A

Figure 7:
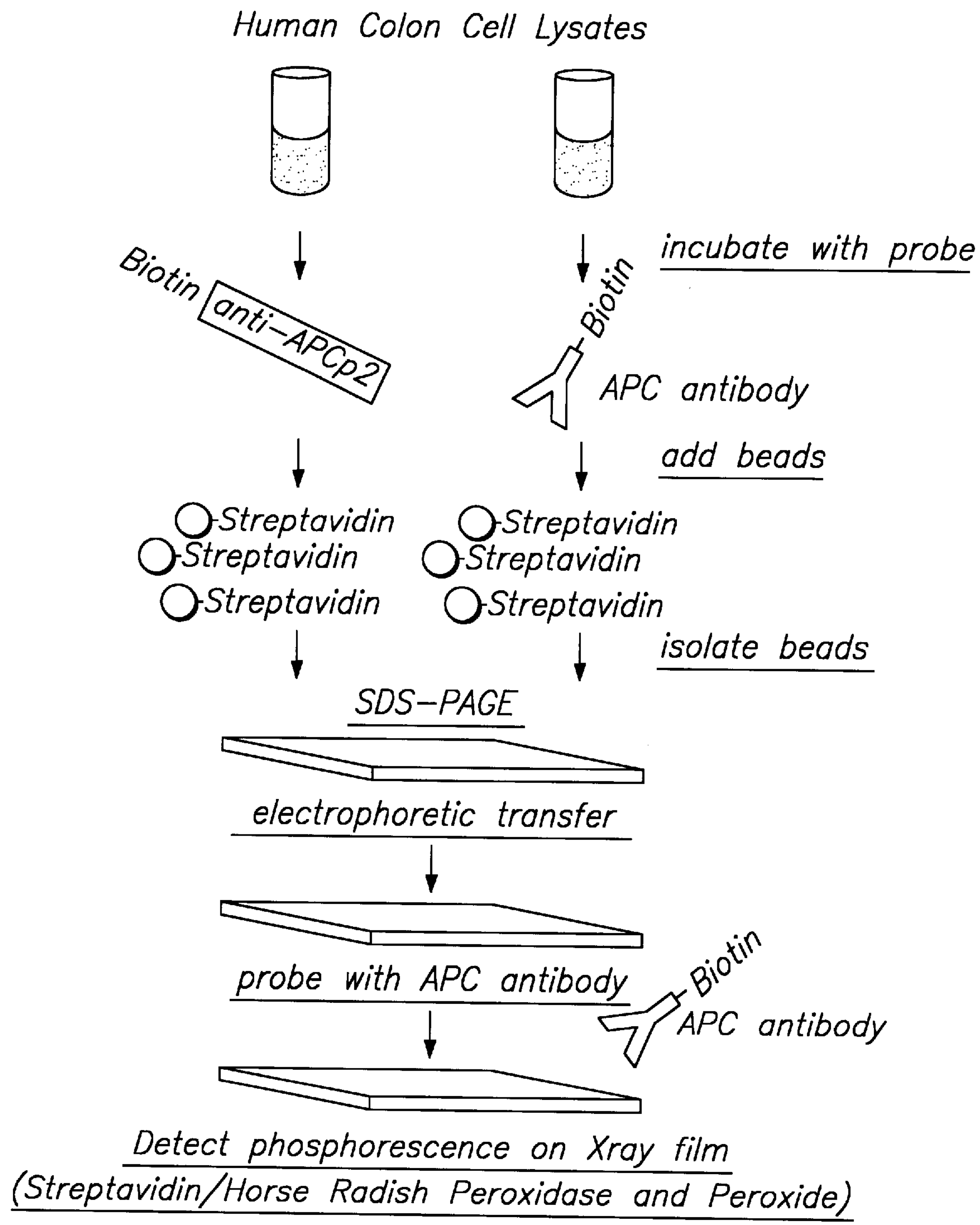
FIG. 7 shows a schematic diagram of precipitation of wild type and mutant APC from human cell lines using biotinylated anti-APCp2 or biotinylated anti-APC monoclonal antibody.
Figure 8A:
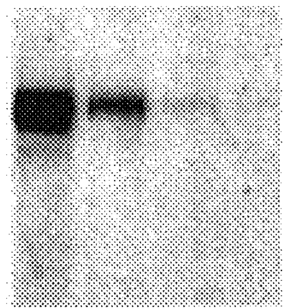
FIG. 8 shows Western blots of wild type and mutant APC from human colon cancer cell lines precipitated using biotinylated anti-APCp2 or biotinylated anti-APC monoclonal antibody.
Figure 8B:
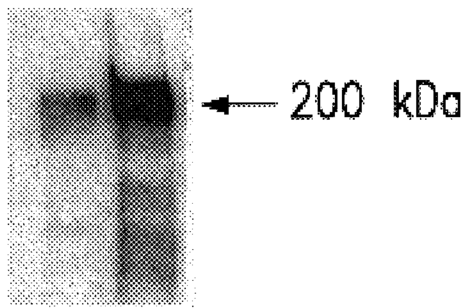
Figure 8C:
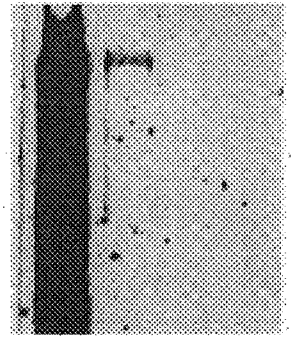
Figure 8D:
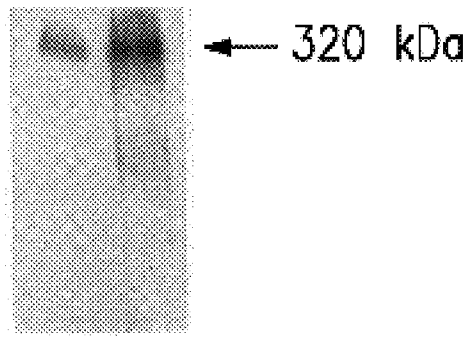

The anti-APC Polypeptide Probe is Sensitive to Low Endogenous in vivo Cellular Concentrations of Human APC Precipitation experiments were carried out in order to determine whether the anti-APCp1 polypeptide probe was capable of detecting the low in vivo levels of APC which are typically present in normal and tumor cells. FIG. 7 is a schematic representation of the strategy used. Briefly, cell lines which produce a normal (i.e., full length human APC) and mutant (i.e., truncated human APC) were lysed, and the lysate combined with either biotinylated anti-APCp2 or biotinylated anti-APC monoclonal antibody. Molecules bound to the biotinylated probes were collected by binding to streptavidin, and the bound molecules released from the beads followed by SDS-PAGE, blotting of the gels, and detection with a biotinylated APC antibody. Phosphorescence was detected on X-ray film. These steps are elaborated in more detail as follows.

A. Cell Lines

1. DLD-1 (ATCC CCL-221):

The DLD-1 cell line expresses an approximately 150 kDa truncated mutant APC in the absences of full-length APC expression. These cells were cultured in RPMI1640 medium (Gibco BRL) supplemented with 10% fetal calf serum (HyClone Laboratories).

2. SW480 (ATCC CCL-228):

The SW480 cell line expresses an approximately 150 kDa truncated mutant APC. While it is generally accepted in the art that SW480 does not express full-length APC protein, faint bands were observed migrating at the size of full-length APC that cross-react with APC antibodies in SW480 Westerns and immunoprecipitations. SW480 cells were cultured in Leibowitz's L-15 medium (Gibco BRL) supplemented with 10% fetal calf serum.

3. LS174T (ATCC CL-188):

The LS174T cell line expresses full-length APC protein. There are no known APC mutations in this cell line. LS174T is thought to be derived from a tumor that arose via the "genetic instability" pathway rather than the APC pathway. This cell line was cultured in Minimal Essential Medium (Gibco BRL) supplemented with 10% fetal calf serum and 1% non-essential amino acids.

B. Probe Precipitation Protocol

1. Lysate Preparation

Cells were harvested at 90–100% confluency. Cells were washed twice with ice-cold Dulbecco's phosphate buffered saline (Gibco BRL) containing magnesium chloride and calcium chloride, scraped into 15 mL ice cold D-PBS and pelleted in a Beckman J-6 centrifuge for 5 minutes at 4° C. The cell pellet was resuspended in 1 mL ice-cold phosphate buffer, pH 8, containing 0.2% NP-40, 400 μg/mL of Pefabloc SC (Boehringer Mannheim) and 10 μg/mL each of leupeptin, pepstatin, and aprotinin. The suspension was sonicated 3×30s at 4° C., then pelleted for 15 minutes at 4° C. in a microcentrifuge. This supernatant, which should contain both nuclear and cytosolic proteins was used for APC precipitation.

2. Precipitation 2 nmol biotinylated probe (B-Probe), unbiotinylated probe (Probe) or D-biotin were added to aliquots of cell lysate (aliquots typically contained 1.5–2 mg total protein by Bradford assay) and incubated with constant rocking for one hour at 4° C. After one hour, 2 mg streptavidin magnetic particles (Boehringer Mannheim) were added to each reaction and incubated, rocking, for one hour at 4° C. Streptavidin magnetic particles were preblocked overnight in lysis buffer containing 2.5% bovine serum and 2.5% casamino acids (Difco). Pellets were washed five times in lysis buffer containing protease inhibitors, and the final supernatant was removed. Subsequently, pellets were incubated for 10 minutes at 95° C. in 20 μL lysis buffer containing 1 mM D-biotin. After 10 minutes, 10 μL SDS-PAGE sample buffer was added to each pellet and reactions were incubated an additional 5 minutes at 95° C. Precipitates were electrophoresed on 6% precast tris-glycine polyacrylamide gel (Novex) electroblotted to nitrocellulose and probed with APC Ab-1 (Oncogene Science) (Smith K J, et al. supra, (1993)) as previously described.

C. Immunoprecipitation of APC protein using anti-APC antibodies

1. Lysate Preparation

Lysates were prepared exactly as described above except that cells were lysed in ice-cold Dulbecco's PBS supplemented with 100 mM KCl, 0.2% NP-40 and protease inhibitors.

2. Immunoprecipitation

Immunoprecipitation of APC was performed essentially as described above. 2.5 μg each of anti-APC Ab-5 and Ab-6 (Oncogene Science) (Smith K J, et al. (1993) *Proc. Natl. Acad. Sci USA* 90, 2846–2850) was added to each lysate aliquot; 2.5 μg of nonspecific mouse IgG1 and IgG2b antibodies were added to separate aliquots as negative controls for the precipitation. Lysates were incubated with antibody for one hour at 4° C., rocking, then 50 μL Protein G Agarose was added to the lysate and allowed to incubate for one hour. (Protein G agarose, 20%w/v, was preblocked overnight with 5% BSA in lysis buffer.) Following five washes with ice-cold lysis buffer, Protein G agarose pellets were resuspended in 15 μL SDS PAGE sample buffer, incubated for 5 minutes at 95° C., then loaded on a 6% precast tris-glycine polyacrylamide gel. Western Blot analysis was performed as described above.

FIG. 8 shows the results of the immunoprecipitation of full-length (two lower blots) and mutant truncated APC-55 forms (two upper blots) from human colon cell lines using either anti-APC antibody or the biotinylated anti-APCp2 polypeptide probe. This data demonstrates the specific binding of anti-APCp2 peptide to both wild-type (320 kDa) and mutant (200 kDa) APC proteins at very low endogenous cell concentrations. Furthermore, this data also demonstrates that the biotinylated monoclonal antibody immunoprecipitations showed a similar band pattern as the designed coiled coil polypeptide probe.

Example 5B

An additional affinity purification protocol was performed with Western blots of precipitations of APC from three different human colon cancer cell lines: 293 (FIG. 9A), which expresses full-length APC, DLD-1 (FIG. 9B), which contains a stop at codon 1417 and expresses a truncated APC molecule of 190 kDa, and HT-29 (FIG. 9C), which expresses two truncated APC molecules of approximately 100 and 200 kDa (Morin et al., *Proc. Natl Acad. Sci. USA* 93: 7950–54 (1996).

Briefly, cells were harvested at 90–100% confluency, washed twice with ice-cold Dulbecco's phosphate buffered saline (D-PBS, Gibco BRL) containing $MgCl_2$ and $CaCl_2$, scraped into 15 ml ice cold D-PBS and pelleted in a Beckman J-6 centrifuge for 5 minutes at 4° C. Cell pellets were resuspended in 1 ml ice-cold phosphate buffer, pH8, containing 0.1% NP-40, 40 μg/ml of Prefabloc SC (Boehringer Mannheim) and 10 μg/ml each of leupeptin, pepstatin and aprotinin.

The suspension was sonicated, then pelleted for 15 minutes at 4° C. in a microcentrifuge. For antibody-mediated precipitations 3 μg of anti-APC Ab1 (Oncogene Science/Calbiochem) or a non-specific mouse $IgG_1$ antibody (Sigma) was added. After 30 min on ice, 50 μL protein-G agarose (preblocked overnight with 5% BSA in lysis bufffer) was added to the lysates and allowed to incubate for one hour, rocking at 4° C. Following five washes with ice-cold lysis buffer, protein G agarose pellets were resuspended in 15 μL SDS PAGE sample buffer and incubated for 5 minutes at 95° C.

For peptide-mediated precipitations, 2 nanomoles biotinylated-anti-APCp1, unbiotinylated anti-APCp 1, or D-biotin were added on ice to aliquots of cell lysate (aliquots typically contain 0.5–1 mg total protein by Bradford assay). One milligram streptavidin magnetic particles (Boehringer Mannheim), preblocked overnight in lysis buffer containing 5% BSA was added to each reaction and incubated, rocking, for one hour at 4° C. Pellets were washed five times in ice-cold lysis buffer and incubated for 10 minutes at 55° C. in 10 μL PBS containing 0.1 mM D-biotin. SDS-PAGE sample buffer (10 μL) was added to each pellet and reactions were incubated 5 minutes at 95° C. Precipitates were electrophoresed on 6% tris-glycine polyacrylamide gel (Novex), electroblotted to nitrocellulose and probed.

Blots were blocked for 1 hour in TBST (10 mM phosphate, 175 mM NaCl, pH 8.0, 0.1% Tween-20) containing 5% BSA and probed with anti-APC antibody Ab-1 (Oncogene Science/Calbiochem), or a monoclonal anti β-catenin antibody (Transduction Laboratories). Anti-APC Ab-1 was diluted 1:150 in TBST, 1% BSA and anti-β-catenin antibody was diluted 1:2000. Blots were washed 3 times for 5 minutes each in TBST and incubated 1 hour in horseradish peroxidase-conjugated rabbit anti-mouse $IgG_1$ antibody (Pierce) diluted 1:30,000 in TBST, 1% BSA. After three 15-minute washes in TBST, blots were developed using ECL substrate (Amersham). Westem blots carried out with antibodies specific for the 20S proteasome p32 subunit (Maine Biotechnology) and E-cadherin (Transduction Laboratories) showed no staining of proteins associated with anti-APCp1 precipitations (data not shown), reflecting the specificity of the antisense peptide for the APC protein.

Figure 9A:
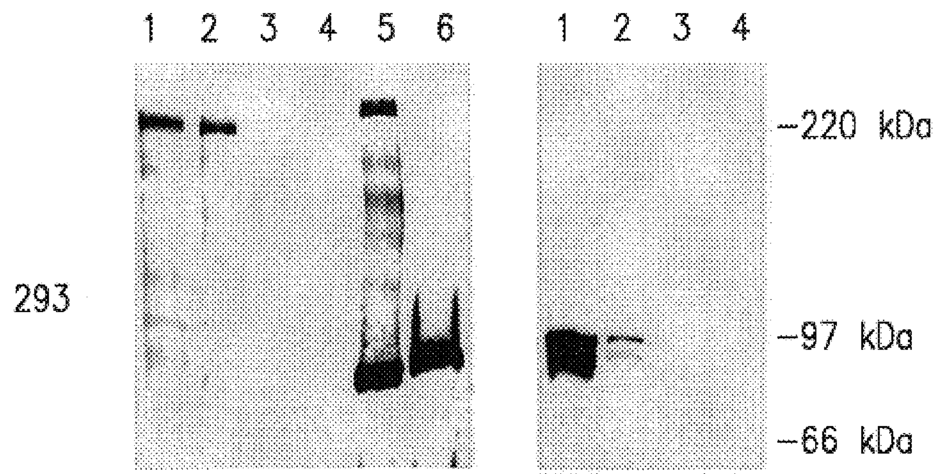
FIGS. 9A–C shows Western blots of precipitations of APC from human colon cancer cell lines 293 (A), DLD-1 (B), and HT-29 (C).
Figure 9B:
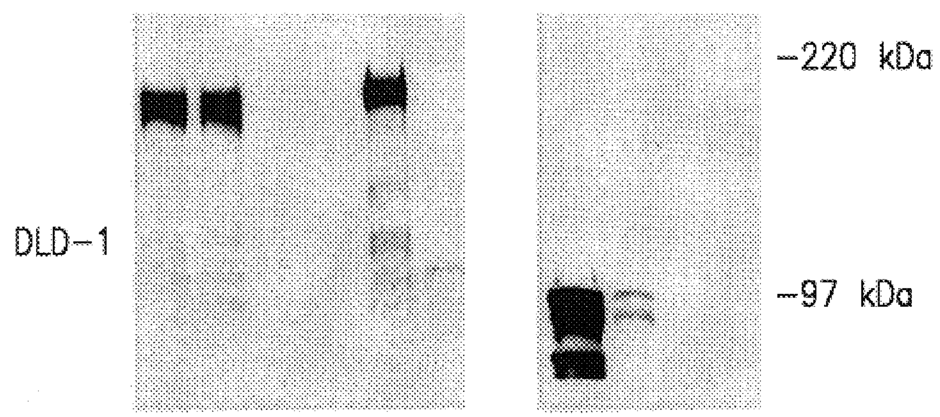
Figure 9C:
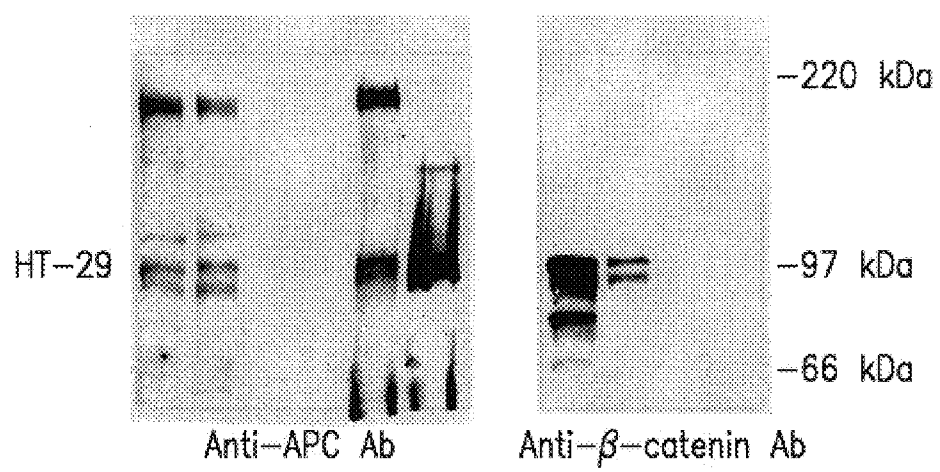

As shown in FIG. 9, blots were probed with an APC antibody (left panels) or a β-catenin antibody (right panels). The total lysate is shown in lane 1. Precipitations were performed using: lane 2, biotinylated-anti-APCp1; lane 3, anti-APCp1 without biotin; lane 4, biotin alone; lane 5, the anti-APC antibody Ab-1; or lane 6, a non-specific mouse IgG. The biotinylated-anti-APCp1 precipitated truncation mutants and full-length APC at endogenous cell concentrations, demonstrating the affinity and specificity of the designed probe. Further, similar patterns and yields of APC polypeptides were captured with biotinylated anti-APCp1 or a biotinylated monoclonal antibody specific for the APC amino terminus (FIG. 9A).

Anti-APCp1 also coprecipitated β-catenin, a protein that recognizes motifs in the central third of the APC sequence (right panels) (Munemitsu (1995); Rubinfeld (1993)). These results suggest that the antisense peptide binds to APC at low endogenous concentrations and pairs with full-length APC polypeptide chains without disrupting APC/β-catenin complexes. Only a subset of β-catenin species coprecipitated from tumor cell lines (FIG. 9), suggesting that anti-APCp1 is specific for APC and APC-associated proteins. Fluorescence energy transfer measurements using fluorescein- and coumarin-labeled anti-APCp1 and APC-55 (respectively) suggest an upper limit for the Kd of the heterodimer of 10 nM (data not shown). Because the amino-terminal, coiled coil sequence targeted by anti-APCp1 occurs in tumor-associated truncation mutants, the distinct electrophoretic mobilities of the species detected by the antisense peptide distinguish wild-type from tumorigenic APC variants (FIG. 9).

In contrast to anti-APCp1, other protein-targeted ligands require experimental selections. Antibodies undergo selection and maturation in vivo, and iterative, system-specific binding assays are necessary to obtain protein ligands from phage display or chemical libraries (D. McGregor, *Mol. Biotechnol.* 6, 155–62 (1996); K. Janda, *Proc. Natl. Acad Sci. USA* 91, 10779–85 (1994)). These experimental methods also necessitate purification of the target protein, and the chemical complexity of the starting library limits the number of ligands screened. In contrast, the method used here to produce anti-APCp1 relies on simple, general pairing rules to design the sequence of a peptide capable of recognizing a target coiled coil.

Like complementary oligonucleotides, antisense coiled coils combine the utility of a sequence-based design and the simplicity of chemical synthesis. Unlike antibodies, the antisense peptides are small, and they require no disulfide bonds for stability, no purification of the target protein and no use of animals. In addition, peptides directed against coiled coils necessarily disrupt the target structure (Goldman et al., *J. Cell Biol.* 134, 971–983 (1996); Olive et al., *J. Biol. Chem.* 271, 2040–2047 (1996); Olive et al., *J. Biol. Chem.* 272, 18586–94 (1997); Sougen et al., *Eur. J Biochem.* 240, 765–773 (1996); Tripet et al., *Prot. Eng.* 9, 1029–1042 (1996)). Coiled coil sequences are readily identified by computer methods (Lupas (1996); Wolf (1997); Berger (1995)), making this large family of proteins amenable to antisense probe design. These distinctive properties suggest that antisense coiled coils may have broad uses in vitro and in vivo.

Example 6

Sequence-Based Design of a Peptide Probe for Residues 6 to 49 of Yeast Tropomyosin (TPM1)

Tropomyosin (TPM1) is essential in yeast for stabilizing actin cables and for cytokinesis. The phenotypes of null mutants and the cellular distribution of tropomyosin have been characterized. The sequence of the cloned gene shows that tropomyosin contains many "violations" of the folding rules described supra in Tables 2–5, which can be compensated in a peptide probe designed in accordance with the pairing rules of Table 2. The target sequence in TPM1 is a coiled coil sequence KLSNLKLEAESWQEKY-EELKEKNKDLEQENVEKENQIKSLTVK (SEQ ID NO: 6). The rationale discussed in the following Table 11 was used to design a probe specific for the TPM1 coiled coil target sequence.

TABLE 11

Sequence-based Design of a Peptide Probe for Residues 6 to 49 of Yeast Tropomyosin (TPM1) Design Rationale

| Position | Residue | Change | Rationale |
|---|---|---|---|
| g | Lys1 | Glu | Stabilize heterodimer (+/− with Lys6) |
| | | | Destabilize Probe homodimer (−/− with Glu6) |
| e | Lys6 | Glu | Stabilize heterodimer (+/− with Lys1) |
| | | | Destabilize Probe homodimer (−/− with Glu1) |
| g | Glu8 | Arg | Heterospecificity (interacts with Gln 13) |
| | | | Destabilize Probe homodimer (+/+ with Lys13) |
| a | Ala9 | Ile | Complement core packing* |
| b | Glu10 | Lys | Increase helical propensity and net charge |
| c | Ser11 | Lys | Increase helical propensity and net charge |
| d | Trp12 | Leu | Complement core packing* |

TABLE 11-continued

Sequence-based Design of a Peptide Probe for Residues 6 to 49 of Yeast Tropomyosin (TPM1) Design Rationale

| Position | Residue | Change | Rationale |
|---|---|---|---|
| e | Gln13 | Lys | Stabilize heterodimer (+/− with Glu8) |
| | | | Destabilize Probe homodimer (+/+ with Lys8) |
| g | Lys15 | Glu | Stabilize heterodimer (+/− with Lys20) |
| | | | Destabilize Probe homodimer (−/− with Glu20) |
| a | Tyr16 | Thr | Complement core packing* |
| b | Glu17 | Lys | Increase helical propensity and net charge |
| | Glu18 | Lys | Increase helical propensity and net charge |
| e | Lys20 | Glu | Stabilize heterodimer (+/− with Lys15) |
| | | | Destabilize Probe homodimer (−/− with Glu15) |
| g | Glu29 | Lys | Stabilize heterodimer (+/− with Glu34) |
| | | | Destabilize Probe homodimer (+/+ with Lys34) |
| a | Asn30 | His | Complement core packing* |
| d | Lys33 | Ala | Complement core packing* |
| e | Glu34 | Lys | Stabilize heterodimer (+/− with Glu29) |
| | | | Destabilize Probe homodimer (+/+ with Lys29) |
| f | Asn35 | Tyr | Chromophore for concentration determination |
| g | Gln36 | Lys | Destabilize Probe homodimer (+/+ with Arg41) |
| e | Thr41 | Arg | Heterospecificity (interacts with Gln36) |
| | | | Destabilize Probe homodimer (+/+ with Lys36) |
| f | Val42 | Glu | Increase solubility |

*Changes based on analysis of keratin coiled-coil sequences.

Based on the above rationale, the following probe is synthesized: ESNLELRIKKLKEETKKLEEKNKDLEQ KHVEAKYKIKSLREK (SEQ ID NO: 7). Changes in the TPM1 sequence are underlined.

Example 7

Sequence-based Design of a Peptide Probe for Residues 846 to 913 of *C. elegans* Dpy-27

Dpy-27 is a component of a complex of proteins required to globally reduce the level of gene expression from the X chromosome in *C. elegans* hermaphrodites. This protein complex localizes to the X-chromosome. The target coiled coil was identified from the Dpy-27 sequence using the program PairCoil. This target Dpy-27 coiled coil had the sequence RMVNYREVTVEDLDEKRA-QIADLKRVQEESQKSSAKIKQQIEQYKRKMFME LVQK (SEQ ID NO: 8). The rationale discussed in the following Table 12 was used to design a probe specific for the Dpy-27 target sequence.

TABLE 12

Sequence-based Design of a Peptide Probe for Residues 846 to 913 of *C. elegans* Dpy-27 Design Rationale

| Position | Residue | Change | Rationale |
|---|---|---|---|
| g | Arg1 | Glu | Stabilize heterodimer (+/− with Arg6) |
| | | | Destabilize Probe homodimer (−/− with Glu6) |
| a | Met2 | Ile | Complement core packing* |
| d | Tyr5 | Phe | Complement core packing* |
| e | Arg6 | Glu | Stabilize heterodimer (+/− with Arg1) |
| | | | Destabilize Probe homodimer (−/− with Glu1) |
| g | Thr9 | Arg | Stabilize heterodimer (+/− with Asp14) |
| | | | Destabilize Probe homodimer (+/+ with Arg14) |
| a | Val10 | Ala | Complement core packing* |
| e | Asp14 | Arg | Destabilize Probe homodimer (+/+ with Arg9) |
| f | Glu15 | Tyr | Chromophore for concentration determination |
| g | Gln19 | Glu | Stabilize heterodimer (+/− with Lys24) |
| | | | Destabilize Probe homodimer (−/− with Glu24) |

TABLE 12-continued

Sequence-based Design of a Peptide Probe for Residues 846 to 913 of *C. elegans* Dpy-27
Design Rationale

| Position | Residue | Change | Rationale |
|---|---|---|---|
| e | Lys24 | Glu | Destabilize Probe homodimer (–/– with Glu19) |
| g | Gln26 | Arg | Destabilize Probe homodimer (+/+ with Arg31) |
| a | Val27 | Ala | Complement core packing* |
| d | Ser30 | Thr | Complement core packing* |
| e | Gln31 | Arg | Destabilize Probe homodimer (+/+ with Arg26) |
| g | Ser33 | Glu | Stabilize heterodimer (+/– with Lys38)<br>Destabilize Probe homodimer (–/– with Glu38) |
| a | Ser34 | Asn | Complement core packing* |
| d | Ile37 | Ala | Complement core packing* |
| e | Lys38 | Glu | Destabilize Probe homodimer (–/– with Glu33) |
| g | Gln40 | Glu | Stabilize heterodimer (+/– with Lys45)<br>Destabilize Probe homodimer (–/– with Glu45) |
| d | Tyr44 | Phe | Complement core packing* |
| e | Lys45 | Glu | Destabilize Probe homodimer (–/– with Glu40) |
| g | Lys47 | Glu | Destabilize Probe homodimer (–/– with Glu52) |
| a | Met48 | Leu | Complement core packing* |
| d | Met51 | Ala | Complement core packing* |
| e | Phe52 | Glu | Stabilize heterodimer (+/– with Lys47)<br>Destabilize Probe homodimer (–/– with Glu47) |
| a | Leu55 | Phe | Complement core packing* |

*Changes based on analysis of keratin coiled-coil sequences.

Based on the above rationale, the following probe is synthesized: EIVNFEEVEVRAYDLREKRAEIADLERRAEE TRKENAKAEQEIEQFERELDRAEMEFVQK (SEQ ID NO: 9). Changes in the DPY-27 sequence are underlined.

Example 8

A Coiled Coil Polypeptide Probe is a Useful Therapeutic Agent Against Infection with HIV Virus Of the anti-human immunodeficiency virus (HIV) treatment strategies tested to date, none is curative and only certain inhibitors of the viral reverse transcriptase (RT) and protease have demonstrated clinical benefit. As a result, the search for new, more efficacious drugs and/or other sites on the virus against which to target antiviral therapy continues at an urgent pace. The trimeric gp41 protein of HIV mediates fusion of the viral and host cell membranes. Trimerization of gp41 is mediated by helical regions comprising amino acids 540–590 and 624–666. Residues 540–590 are thought to form a central three-helical coiled coil onto which amino acids624 associate (M. Lu, S. C. Blacklow and P. S. Kim, (1995), *Nature Structural Biology,* 2: 1075–1082).

This Example describes the generation of a coiled coil polypeptide capable of binding specifically to a coiled coil protein, the HIV gp41 protein, which is located on the surface of HIV and which may be useful as an antiretroviral agent. This Example involved (A) the design and synthesis of a coiled coil polypeptide which binds specifically to HIV gp41 protein, and (B) using the coiled coil polypeptide to inhibit in vitro viral activity.

A. Design and Synthesis of a Coiled Coil Polypeptide Which Binds Specifically to HIV gp41 Protein The target coiled coil identified in gp41 of HIV has the sequence: QARQLLSGIVQQQNNLL-RAIEAQQHLLQLTVWGIKQLQARILAVERYLKDQQ LLGIW (SEQ ID NO: 10).

The rationale discussed in the following Table 13 was used to design a probe specific for the gp41 sequence.

TABLE 13

Sequence-based Design of a Peptide Probe for Residues 540 to 596 of HIV gp41
Design Rationale

| Position | Residue | Change | Rationale |
|---|---|---|---|
| d | Ala2 | Leu | Complement core packing*, favor dimerization |
| a | Leu6 | Met | Complement core packing* |
| d | Ile9 | Ala | Complement core packing*, favor dimerization |
| g | Gln12 | Glu | Destabilize Probe homodimer (-l- with Glu17) |
| a | Gln13 | Val | Complement core packing*, favor dimerization |
| e | Leu17 | Glu | Destabilize Probe homodimer (-l- with Glu12) |
| g | Ala19 | Glu | Destabilize Probe homodimer (-l- with Glu24) |
| a | Ile20 | Val | Complement core packing* |
| d | Gln23 | Met | Complement core packing* |
| e | Gln24 | Glu | Destabilize Probe homodimer (-l- with Glu19) |
| g | Leu26 | Thr | Favor dimerization**, improve solubility |
| a | Leu27 | Ile | Complement core packing* |
| d | Thr30 | Ser | Complement core packing* |
| e | Val31 | Gln | Favor dimerization**, enhance solubility |
| f | Trp32 | Lys | Enhance solubility |
| g | Gly33 | Glu | Destabilize probe homodimer (-l- with Glu38) |
| a | Ile34 | Val | Complement core packing* |
| d | Leu37 | Ala | Complement core packing* |
| e | Gln38 | Glu | Destabilize Probe homodimer (-l- with Glu33) |
| f | Ala39 | Asn | Enhance solubility |
| a | Ile41 | Val | Complement core packing* |
| d | Val44 | Met | Complement core packing* |
| g | Tyr47 | Glu | Destabilize Probe homodimer (-l- with Glu52) |
| a | Leu48 | Val | Complement core packing* |
| d | Gln51 | Met | Complement core packing* |
| e | Gln52 | Glu | Destabilize Probe homodimer (-l- with Glu47) |
| f | Leu53 | Asn | Enhance solubility |
| a | Gly55 | Ile | Complement core packing* |
| d | Ala2 | Leu | Complement core packing*, favor dimerization |
| a | Leu6 | Met | Complement core packing* |
| b | Ile56 | Glu | Enhance solubility |
| c | Trp57 | Tyr | Enhance solubility, introduce chromophore |

*Changes based on analysis of keratin coiled-coil sequences
**D. N. Woolfson and T. Alber (1995), Protein Science, 4: 1596–1607.

Based on the above rationale, the following anti-gp41 probe is synthesized: QLRQLMSGAVQEVNNLEREVEA MEHTIQLSQKEVKQAENRVLAMEREVKD MENL IEY(SEQ ID NO: 11). Changes in the GP41 sequence are underlined. This anti-gp41 coiled coil sequence is aimed at preventing assembly of the gp41 trimer by preferentially forming a heterodimer with residues 540–596. The specificity of the coiled coil polypeptide for the gp41 protein is confirmed using circular dichroism, equilibrium ultracentifugation, and native acrylamide gel electrophoreses as described supra in Example 3.

B. Using the Coiled Coil Polypeptide for Inhibition of in vitro Viral Activity

The efficacy of the coiled coil polypeptide (which is synthesized as described in the preceding section) in treating HIV infection is investigated by the determination of the inhibitory effect of different concentrations of the coiled coil polypeptide on the formation of viral induced syncytia formation and on infection by cell-free virus in vitro. These steps are described below.

1. Inhibition of Infected Cell-Induced Syncytium Formation By the Coiled Coil Polypeptide Serial concentrations of coiled coil polypeptide 0 (e.g., between 1–50 $\mu$g/ml) are tested for blockade of the cell fusion process which is induced by HIV. The HIV-$1_{LAI}$ virus (Popovic et al. (1984) *Science* 224:497–5080) is prepared as follows. HIV-$1_{LAI}$ virus is propagated in CEM cells cultured in RPM1 1640 containing 10% fetal bovine serum. Supernatant from the infected CEM cells is passed through a 0.2-$\mu$m filter and the infectious titer is estimated in a microinfectivity assay using the AA5 cell line to support virus replication. For this purpose, 25 $\mu$l of serially diluted virus is added to 75 $\mu$l of AA5 cells at a concentration of $2\times10^5$ per ml in a 96-well microtiter plate. Each virus dilution is tested in triplicate. Cells are cultured for 8 days by addition of fresh medium every other day. On day 8 postinfection, supernatant samples are tested for virus replication as evidenced by RT activity. The 50% tissue culture infectious dose ($TCID_{50}$) is calculated. The titer of the HIV-$1_{LAI}$ stock used for these investigations, as measured on the AA5 cell line, is expected to be $10^7 TCID_{50}$ml. The two primary isolates are obtained from peripheral blood mononuclear cells (PB-MCs) of two infected donors, one from Brazil (HIV-$1_{Br3}$) and the other from Trinidad (HIV-$1_{QZ2775}$), by cocultivation with phytohemagglutinin-stimulated normal donor PBMCs in RPMI 1640 containing interleukin 2. The infectious titers of the primary virus stocks are estimated by titration on phytohemagglutinin-stimulated normal human PBMCs in a 96-well microtiter plate, again by using RT activity released to the supernatant as evidence of successful infection. The infectious titer of both these isolates is estimated to be $=10^3$ $TCID_{100}$/ml.

The virus is ultracentrifuged to remove non-virus-associated peptides or soluble CD4 as follows. A 0.4-ml sample of treated virus is layered onto 0.15 ml of phosphate-buffered saline containing 5% sucrose in a Beckman SW50 minitube (total capacity about 0.6 ml) and centrifuged at 35,000 rpm for 60 min at 4° C. The supernatant is aspirated and the virus pellet is resuspended in RPMI 1640 containing 10% fetal bovine serum.

The prepared virus is used in the cell fusion assay as follows. MOLT-4 cells ($=7\times10^4$) are incubated with CEM cells ($10^4$) chronically infected with HIV-$1_{LAI}$ in 96-well plates (half-area cluster plates; Costar) in 100 $\mu$l of culture medium. Peptide inhibitors are added in 10 $\mu$l and the cell mixtures are incubated for 24 hr at 37° C. At that time, multinucleated giant cells are estimated by microscopic examination ×40 magnification, which allowed visualization of the entire well in a single field. Protection from viral induce cell-cell fusion indicates that the coiled coil polypeptide is useful for antiviral therapy.

2. Inhibition of Infection By Cell-Free Virus Using the Coiled Coil Polypeptide

The ability of the coiled coil polypeptide to inhibit infection by cell free virus is used as an in vitro assay of the polypeptide's efficacy in the prevention and treatment of HINV infection in vivo. A range of concentrations (0–100 $\mu$g/ml) of the coiled coil polypeptide is incubated in triplicate with virus (about 500 $TCID_{50}$) and cells in 96-well microtiter plates for 8 days. On the 8th day, supernatant is tested for revise transcriptase (RT) activity as evidence of successful infection. A RT microassay is used. Supernatants from virus/cell cultures are made 1% (vol/vol) in Triton X-100. A 10-$\mu$l sample of supernatant is added to 50 $\mu$l of RT cocktail in a 96-well U-bottom microtiter plate and incubated at 37° C. for 90 min. The cocktail contains 75 mM KCl, 2 mM dithiothreitol, 5 mM $MgCl_2$, poly(A) (5 $\mu$g/ml: Pharmacia cat. no. 27-4110-01), oligo(dT) (0.25 unit/ml; Pharmacia cat. no. 27-7858-01), 0.05% Nonidet P-40, 50 mM Tris-HCl (pH 7.8), 0.5 $\mu$M nonradioactive dTTP, and [$\alpha$.$^{32}$P]dTTP (10 $\mu$Ci/ml; Amersham cat. no. PB.10167; 1 Ci=37 GBq). After incubation, 40 $\mu$l of reaction mixture is applied to a Schleicher & Schuell NA45 membrane (or Whatman DE81 paper) saturated in 2×SSC (0.3 M NaCl/30 mM sodium citrate, pH7) in a Schleicher & Schuel Minifold over one sheet of GB003 filter paper. Each well of the minifold is washed four times with 200 $\mu$l of 2×SSC. The membrane is removed and washed twice in a Pyrex dish with an excess of 2×SSC. Finally the membrane is drained on absorbent paper, placed on Whatman no. 3 paper, covered with SaranWrap, and exposed to film overnight.

The reduction or absence of RT activity in sample treated with the coiled coil polypeptide as compared to controls which are not treated with the coiled coil polypeptide indicate that the coiled coil peptide which is specific for the HINV gp41 polypeptide is useful for antiviral therapy and/or prevention.

ADVANTAGES OF THE PRESENT INVENTION

Traditional biological approaches to the study of disease are limited by the ability of existing nucleic acid-based probed to target only nucleic acids. While antibody-based probes partly overcome this problem in that they target polypeptide sequences, antibodies are both expensive and time-consuming to produce since they require purification of the target polypeptide and maintenance of animals. Moreover, functional antibodies cannot be expressed in intracellular compartments, and their use as biological probes often suffers from varying degrees of antigen expression, non-specific binding and adverse immunogenic reactions.

As is apparent from the data presented herein, the present invention solves the problems encountered in the prior art. The methods of the present invention provide the advantage that any polypeptide products which contains a coiled coil region, and which is involved in any disease state may be specifically and exclusively targeted to the exclusion of other polypeptides. The methods of the present invention provide simple and inexpensive methods for the design and production of polypeptide probes; probe sequence design is based on the simple selection of preferred amino acid pairs, and production is based on routine and automated chemical polypeptide synthesis or recombinant expression systems. Moreover, coiled-coil polypeptides in their native state may be easily targeted using the methods of this invention without the necessity for further purification or manipulations. Additionally, the methods of the present invention are sensitive in that they are capable of detecting physiologically relevant endogenous cellular concentrations of polypeptides.

Accordingly, it is to be understood that the drawings and descriptions in this disclosure are proffered to facilitate the comprehension of the invention and should not be construed to limit the scope thereof. Other improvements and modifications which become apparent to persons of ordinary skill in the art only after reading this disclosure, the drawings and the following claims are deemed within the spirit and scope of the present invention.

All publications and patent applications cited in this specification are herein incorporated by reference as if each individual publication or patent application were specifically and individually indicated to be incorporated by reference.

We claim:

1. A heterospecific polypeptide probe for a target polypeptide having a known amino acid sequence, comprising a substantially purified polypeptide comprising at least one probe coiled coil region capable of heterospecific oligomerization with a target coiled coil region in said target polypeptide, wherein the polypeptide sequence of said probe coiled coil region differs from the polypeptide sequence of said target coiled coil region with respect to at least one core residue.

2. A probe according to claim 1, wherein the polypeptide sequence of said probe coiled coil region differs from the polypeptide sequence of said target coiled coil region with respect to at least one edge residue such that the charge on the edge residues in said probe coiled coil region is the same and is different from the charge on the edge residues in said target coiled coil region.

3. A probe according to claim 1, wherein the hetero-oligomer between said probe coiled coil region and said target coiled coil region is more stable than the homo-oligomers formed by either said probe coiled coil region or said target oled coil region based on measurement of melting temperature at a fixed total protein concentration or dissociation constant (Kd).

4. A hetero-oligomer formed between a heterospecific polypeptide probe according to any of claims 1–3 and a target polypeptide.

5. A method for making a heterospecific polypeptide probe capable of heterospecific oligomerization with a target polypeptide having a known amino acid sequence, comprising:

providing a probe polypeptide having a probe coiled coil region corresponding to a target coiled coil region of said target polypeptide, wherein the polypeptide sequence of said probe coiled coil region differs from the polypeptide sequence of said target coiled coil region with respect to at least one core residue.

6. The method of claim 5, wherein said probe polypeptide sequence is selected so as to optimize the packing and polarity of the core residues in said probe coiled coil region and in said target coiled coil region.

7. An isolated polynucleotide sequence encoding the polypeptide of claims 1 or 2.

8. A method for detecting a target polypeptide having a known amino acid sequence with at least one target coiled coil region, comprising:

contacting a sample suspected of containing said target polypeptide with a probe polypeptide having a probe coiled coil region capable of heterospecific oligomerization with said target coiled coil region of said target polypeptide; wherein the polypeptide sequence of said probe coiled coil region differs from the polypeptide sequence of said target coiled coil region with respect to at least one core residue; and detecting the formation of said hetero-oligomer.

* * * * *

UNITED STATES PATENT AND TRADEMARK OFFICE
CERTIFICATE OF CORRECTION

PATENT NO. : 6,303,317 B1
DATED : October 16, 2001
INVENTOR(S) : Thomas C. Alber et al.

It is certified that error appears in the above-identified patent and that said Letters Patent is hereby corrected as shown below:

Column 5,
Line 23, change "ITIBS" to -- TIBS --.

Column 12,
Line 13, change "ITIBS" to -- TIBS --.

Column 13,
Line 65, change "a" to -- α --.

Column 14,
Line 4, after 'residues in', change "a" to -- α --.

Column 15,
Line 16, change "1" to -- e --.

Column 32,
Line 48, change "NaPO'₄" to -- $NaPO_4$ --.

Column 38,
Line 29, after 'synthesized: E' insert -- L --.

Signed and Sealed this

Ninth Day of April, 2002

Attest:

JAMES E. ROGAN
*Director of the United States Patent and Trademark Office*

*Attesting Officer*

SEQUENCE LISTING

<160> NUMBER OF SEQ ID NOS: 11

<210> SEQ ID NO 1
<211> LENGTH: 55
<212> TYPE: PRT
<213> ORGANISM: Homo sapiens

<400> SEQUENCE: 1

Met Ala Ala Ala Ser Tyr Asp Gln Leu Leu Lys Gln Val Glu Ala Leu
1 5 10 15

Lys Met Glu Asn Ser Asn Leu Arg Gln Glu Leu Glu Asp Asn Ser Asn
20 25 30

His Leu Thr Lys Leu Glu Thr Glu Ala Ser Asn Met Lys Glu Val Leu
35 40 45

Lys Gln Leu Gln Gly Ser Ile
50 55

<210> SEQ ID NO 2
<211> LENGTH: 54
<212> TYPE: PRT
<213> ORGANISM: Artificial Sequence
<220> FEATURE:
<223> OTHER INFORMATION: Description of Artificial Sequence: synthetic.

<400> SEQUENCE: 2

Met Ala Ala Lys Gly Asp Gln Leu Lys Lys Glu Val Glu Ala Leu Glu
1 5 10 15

Tyr Glu Asn Ser Asn Leu Arg Lys Lys Leu Glu Asp His Lys Lys Lys
20 25 30

Leu Thr Lys Leu Lys Thr Glu Ile Ser Asn Ala Lys Lys Met Leu Lys
35 40 45

Gln Leu Tyr Ala Ser Ile
50

<210> SEQ ID NO 3
<211> LENGTH: 54
<212> TYPE: PRT
<213> ORGANISM: Artificial Sequence
<220> FEATURE:
<223> OTHER INFORMATION: Description of Artificial Sequence: synthetic.
<221> NAME/KEY: SITE
<222> LOCATION: (1)
<223> OTHER INFORMATION: the X at position 1 codes for norleucine.
<221> NAME/KEY: SITE
<222> LOCATION: (46)
<223> OTHER INFORMATION: the X at position 46 codes for norleucine.

<400> SEQUENCE: 3

Xaa Ala Ala Lys Gly Asp Gln Leu Lys Lys Glu Val Glu Ala Leu Glu
1 5 10 15

Tyr Glu Asn Ser Asn Leu Arg Lys Lys Leu Glu Asp His Lys Lys Lys
20 25 30

Leu Thr Lys Leu Lys Thr Glu Ile Ser Asn Ala Lys Lys Xaa Leu Lys
35 40 45

Gln Leu Tyr Ala Ser Ile
50

<210> SEQ ID NO 4
<211> LENGTH: 46
<212> TYPE: DNA
<213> ORGANISM: Artificial Sequence -continued

```
<220> FEATURE:
<223> OTHER INFORMATION: Description of Artificial Sequence: synthetic.

<400> SEQUENCE: 4

tgtaaaacga cggccagtgg aattcatatg gctgcagctt cagttg                46


<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence: synthetic.

<400> SEQUENCE: 5

caggaaacag ctatgaccga attcctaaat acttccttgt agttgttta             49


<210> SEQ ID NO 6
<211> LENGTH: 43
<212> TYPE: PRT
<213> ORGANISM: yeast

<400> SEQUENCE: 6

Lys Leu Ser Asn Leu Lys Leu Glu Ala Glu Ser Trp Gln Glu Lys Tyr
  1               5                  10                  15

Glu Glu Leu Lys Glu Lys Asn Lys Asp Leu Glu Gln Glu Asn Val Glu
             20                  25                  30

Lys Glu Asn Gln Ile Lys Ser Leu Thr Val Lys
         35                  40


<210> SEQ ID NO 7
<211> LENGTH: 43
<212> TYPE: PRT
<213> ORGANISM: Artificial Sequence
<220> FEATURE:
<223> OTHER INFORMATION: Description of Artificial Sequence: synthetic.

<400> SEQUENCE: 7

Glu Leu Ser Asn Leu Glu Leu Arg Ile Lys Lys Leu Lys Glu Glu Thr
  1               5                  10                  15

Lys Lys Leu Glu Glu Lys Asn Lys Asp Leu Glu Gln Lys His Val Glu
             20                  25                  30

Ala Lys Tyr Lys Ile Lys Ser Leu Arg Glu Lys
         35                  40


<210> SEQ ID NO 8
<211> LENGTH: 55
<212> TYPE: PRT
<213> ORGANISM: c. elegans hermaphrodites

<400> SEQUENCE: 8

Arg Met Val Asn Tyr Arg Glu Val Thr Val Glu Asp Leu Asp Glu Lys
  1               5                  10                  15

Arg Ala Gln Ile Ala Asp Leu Lys Arg Val Gln Glu Glu Ser Gln Lys
             20                  25                  30

Ser Ser Ala Lys Ile Lys Gln Gln Ile Glu Gln Tyr Lys Arg Lys Met
         35                  40                  45

Phe Met Glu Leu Val Gln Lys
     50                  55


<210> SEQ ID NO 9
<211> LENGTH: 60
<212> TYPE: PRT
```

-continued

```
<213> ORGANISM: Artificial Sequence
<220> FEATURE:
<223> OTHER INFORMATION: Description of Artificial Sequence: synthetic.

<400> SEQUENCE: 9

Glu Ile Val Asn Phe Glu Glu Val Glu Val Arg Ala Tyr Asp Leu Arg
  1               5                  10                  15

Glu Lys Arg Ala Glu Ile Ala Asp Leu Glu Arg Arg Ala Glu Glu Thr
             20                  25                  30

Arg Lys Glu Asn Ala Lys Ala Glu Gln Glu Ile Glu Gln Phe Glu Arg
         35                  40                  45

Glu Leu Asp Arg Ala Glu Met Glu Phe Val Gln Lys
     50                  55                  60


<210> SEQ ID NO 10
<211> LENGTH: 57
<212> TYPE: PRT
<213> ORGANISM: viral

<400> SEQUENCE: 10

Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
             20                  25                  30

Gly Ile Lys Gln Leu Gln Ala Arg Ile Leu Ala Val Glu Arg Tyr Leu
         35                  40                  45

Lys Asp Gln Gln Leu Leu Gly Ile Trp
     50                  55


<210> SEQ ID NO 11
<211> LENGTH: 57
<212> TYPE: PRT
<213> ORGANISM: Artificial Sequence
<220> FEATURE:
<223> OTHER INFORMATION: Description of Artificial Sequence: synthetic.

<400> SEQUENCE: 11

Gln Leu Arg Gln Leu Met Ser Gly Ala Val Gln Glu Val Asn Asn Leu
  1               5                  10                  15

Glu Arg Glu Val Glu Ala Met Glu His Thr Ile Gln Leu Ser Gln Lys
             20                  25                  30

Glu Val Lys Gln Ala Glu Asn Arg Val Leu Ala Met Glu Arg Glu Val
         35                  40                  45

Lys Asp Met Glu Asn Leu Ile Glu Tyr
     50                  55
```